(12) United States Patent
Mashava

(10) Patent No.: US 6,258,839 B1
(45) Date of Patent: Jul. 10, 2001

(54) ISOLATION OF NATURALLY OCCURING ISOFLAVANONE AND SOME CLINICAL USES THEREOF

(76) Inventor: Peter Mashava, P.O. Box 1116, Harare (ZW)

(*) Notice: Subject to any disclaimer, the term of this patent is extended or adjusted under 35 U.S.C. 154(b) by 0 days.

(21) Appl. No.: 08/998,422

(22) Filed: Dec. 24, 1997

(51) Int. Cl.$^7$ ................... A61K 31/365; C07D 311/04
(52) U.S. Cl. ................... 514/456; 546/135; 548/463; 548/525; 549/60; 549/289; 549/472
(58) Field of Search ................... 549/289; 514/456

(56) References Cited

PUBLICATIONS

Maillard et al., An Antifungal Isoflavanone and a Structure Rev. of a Flavonone from Erythrina, Planta Med. 55(3), 281–282, 1989.*

* cited by examiner

Primary Examiner—Johann Richter
Assistant Examiner—Taofiq A. Solola
(74) Attorney, Agent, or Firm—Jerome J. Norris

(57) ABSTRACT

A compound of general formula I

Formula I

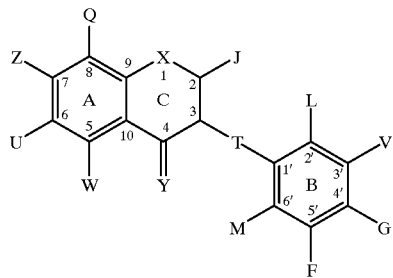

in which the 2–3 bond in ring C could be double or single bond. Ring B and its substituents may be attached at position 2 (at J) in ring C. The key feature in the modifications is that the prenylation must not cyclize through the free OH groups(s) at ortho position to the prenylation. Atoms attached at X in ring C may be S or N or P or C or O or pharmaceutically acceptable metal or $CH_2$. Atoms attached to Y could be S or N or P or O or alkyl ($C_1$–$C_8$) or alkoxy ($C_1$–$C_8$) or alkylthio ($C_1$–$C_8$) or aryloxy ($C_6$–$C_{10}$) or alkoxycarbonyl ($C_2$–$C_8$) or heterocycloalkoxy ($C_2$–$C_{10}$) pharmaceutically acceptable metal or $CH_2$ or the like; the prenylation could be attached at any position L or V or G or F or M or W or U or Z or Q; the prenylation could be singly or multiple or in combination; the prenylation could be penteny group (—$CH_2$—CH=C($CH_3$)$_2$) or geranyl (—$CH_2$CH=C(Me)$CH_2CH_2$CH=C(Me$_2$) or lavandulyl (—$CH_2$—CH(C($CH_3$)=$CH_2$)$CH_2$CH=C($CH_3$)$_2$} or -o- pentenyl (o-$CH_2$—CH=C($CH_3$)$_2$) or -o- geranyl (o-$CH_2$CH=C(Me)$CH_2CH_2$=CH(Me)$_2$) or o-lavandulyl {-o-$CH_2$—CH(C($CH_3$)=$CH_2$)$CH_2$CH=C($CH_3$)$_2$} or substituted pentenyl, geranyl and lavandulyl with hydroxy, alkoxy ($C_1$–$C_8$), alkylthio ($C_1$–$C_8$), aryloxy ($C_6$–$C_{10}$), alkoxycarbonyl ($C_2$–$C_8$) or heterocycloalkoxy ($C_2$–$C_{10}$) or halogen; on the ortho positions of the above groups could be substituted with veratryl or anisyl or epoxyangelyl or isobutanolyl or angelyl or 6-dimethylpyrane or formylloxy or isoamyl or 3-methylbutyl or -o-heterocycle ($C_2$–$C_{10}$) or alkoxy ($C_1$–$C_8$) or alkylthio ($C_1$–$C_8$) or aryloxy ($C_6$–$C_{10}$) or alkoxycarbonyl($C_2$–$C_8$) or heterocycloalkoxy ($C_2$–$C_{10}$) or amino ($NH_2$) or glycosides (1–10 sugar units) or o-glycosides (1–10 units) or oxyacetic acids or Schiff base or dialkylaminoalkyl ($C_1$–$C_{10}$) or amino acid esters or flavan or substituted aryl groups with alkyl ($C_1$–$C_{10}$) or phenoxy or alkenyl ($C_3$–$C_8$) or phenyl substituted with one to three groups, these being hydroxy, halogen, alkynyl ($C_2$–$C_8$) or nitro or cyano or acetates, any position L or V or G or F or M or W or U or Z or Q which are not substituted with the prenylation as above may be substituted such as to prevent internal cyclization of the of the prenylation, groups which can be attached to L or V or G or F or M or W or U or Z or Q could be alkoxy ($C_1$–$C_8$) alkylthio ($C_1$–$C_8$), aryloxy ($C_6$–$C_{10}$), alkoxycarbonyl ($C_2$–$C_8$) or heterocycloalkoxy ($C_2$–$C_{10}$) or halogen or veratryl or anisyl or epoxyangelyl or isobutanolyl or angelyl or 6-dimethylpyrane or formylloxy or isoamyl or 3-methylbutyl or o-heterocycle ($C_2$–$C_{10}$) or alkoxy ($C_1$–$C_8$) or alkylthio ($C_1$–$C_8$) or aryloxy ($C_6$–$C_{10}$) or alkoxycarbonyl($C_2$–$C_8$) or heterocycloalkoxy ($C_2$–$C_{10}$) or amino ($NH_2$) or glycosides (1–10 sugar units) or o-glycosides (1–10 units) or oxyacetic acids or Schiff base or dialkylaminoalkyl ($C_1$–$C_{10}$) or amino acid esters ($C_1$–$C_{10}$) or extended amines ($C_1$–$C_{10}$, $N_1$–$N_6$) or sulphate esters or flavan or substituted flavan or substituted aryl groups with alkyl($C_1$–$C_{10}$) or phenoxy or alkenyl ($C_3$–$C_8$) or phenyl substituted with one to three groups; these being hydroxy (except ortho to prenylation), halogen, or alkynl ($C_2$–$C_8$) or nitro or cyano or acetates or saturated or unsaturated aliphatic ($C_2$–$C_8$), cycloaliphatic ($C_1$–$C_{15}$) or aromatic hydrocarbonyl ($C_1$–$C_{15}$) or bridged cycloalkyl ($C_1$–$C_{10}$) or cycloakenyl ($C_1$–$C_{10}$) or furanylalkyl ($C_1$–$C_{15}$) alkylthioalkyl ($C_5$–$C_{15}$) or alkylene ($C_4$–$C_{10}$) or indolyl or pyridinyl or pyrrolinyl or quinolinyl or thienyl or tert-butoxycarbonyl amino or hydrogen or hydroxy protecting groups or functional groups which increase water solubility of the analog or amino protecting group or sulfhydryl protecting group or carbamat ($C_2$–$C_6$) or heteroaryl or crotyl.

3 Claims, 33 Drawing Sheets

FIG. 1

Isolation of PMZ-1 from Bolusanthus speciosus (SB)

```
                    250 gm Biomass
                         │ methylene chloride:methanol
                         │      (4:1)  overnight
                         ▼
              19.5 gm (7.8%) Crude Extract
                         │  Flash  a) Silica gel
                         │         b) RP - 18
                         ▼
              3.8 gm (19.5%) Fraction of PMZ-1
                         │  MPLC  a) Silica gel
                         │        b) RP - 18
                         ▼
              1.83 gm (48.1%) Fraction of PMZ-1
                         │  HPLC  a) Silica gel
                         │        b) RP - 18
                         ▼
              1.37 gm (74.9%) Pure PMZ-1
```

Overall yields: 0.55% (from biomass), 7.0% (from crude extract)

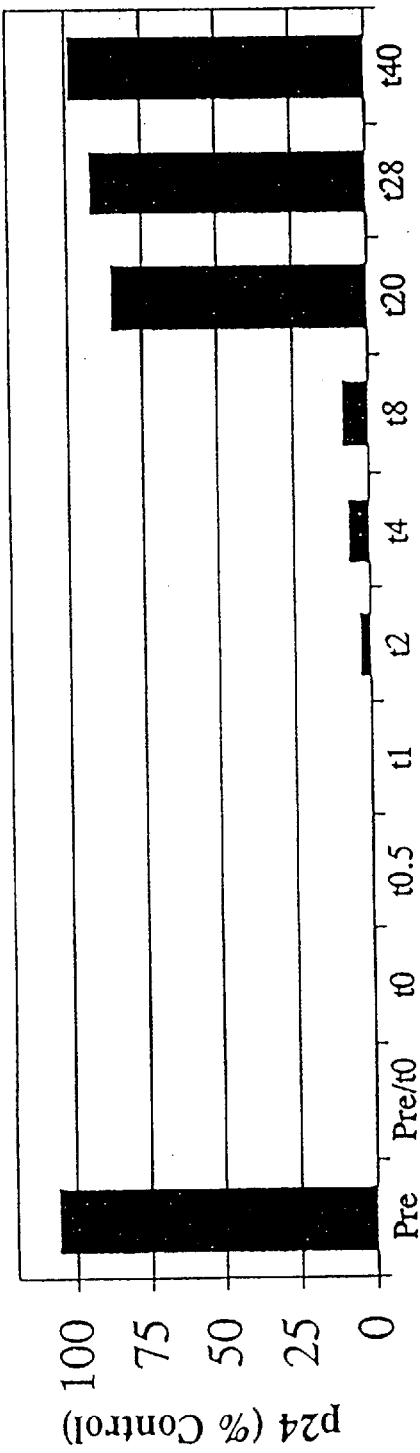
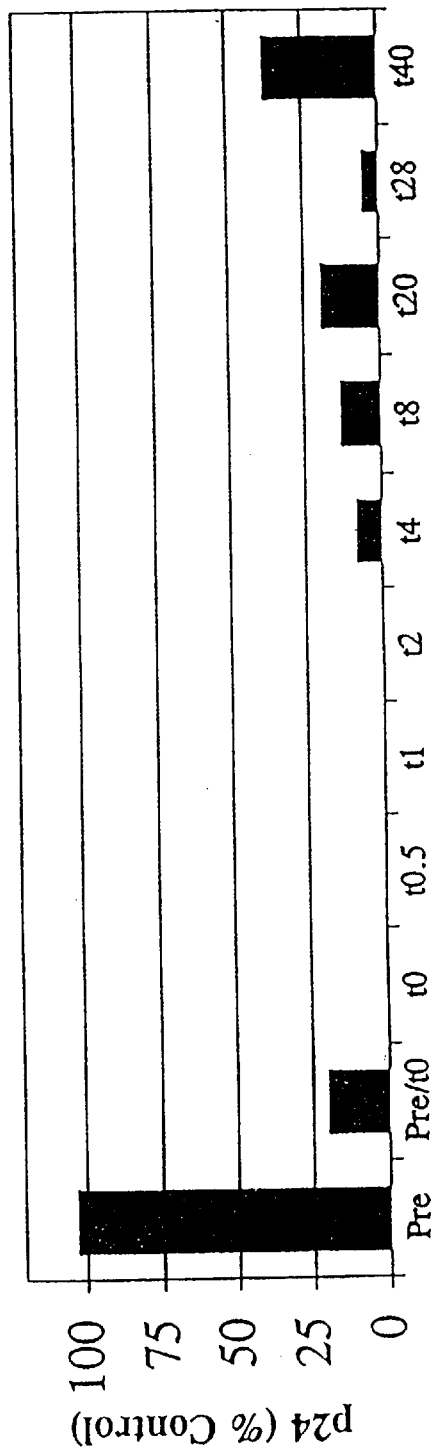
FIG. 16a Nevirapine
FIG. 16b PMZ-1

──▲── VIRAL p24  ──●── CELL VIABILITY

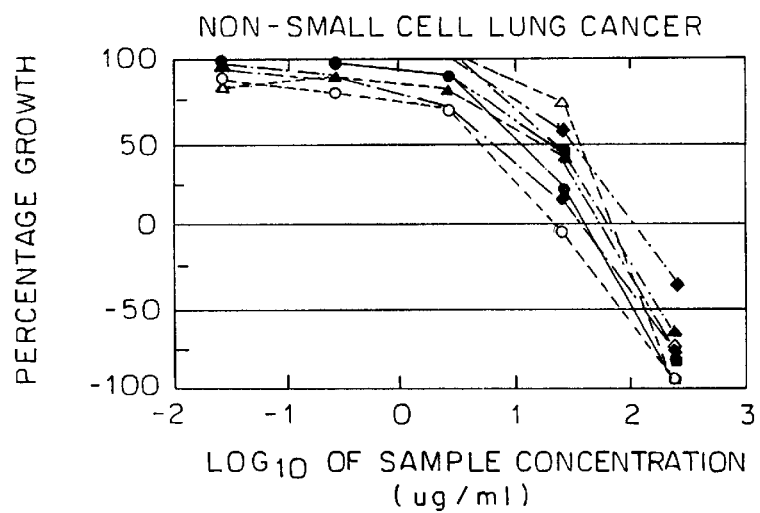
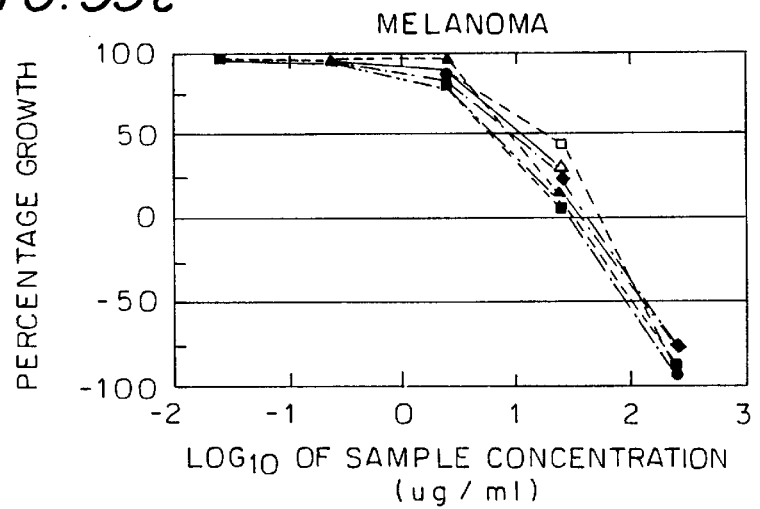
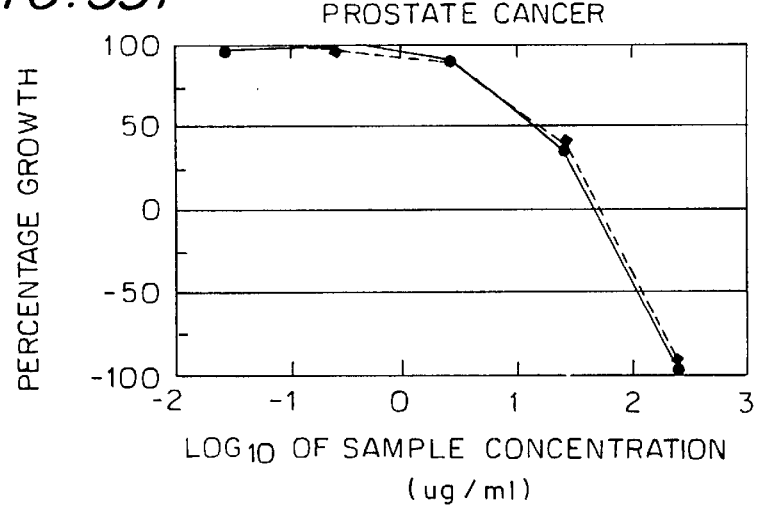

US 6,258,839 B1

ISOLATION OF NATURALLY OCCURING ISOFLAVANONE AND SOME CLINICAL USES THEREOF

TECHNICAL FIELD OF THE INVENTION

The present invention relates to the extraction and purification of a dihydo-isoflavonone from the stem bark, the root and the leaves of *Bolusanthus speciosus* (Bolus) Harms belonging to the plant family Fabaceae: Fabiodeae; identification of the structure of the dihydro-isoflavonone isolated to the potential clinical applications of the pure dihydo-isoflavonone as anti-HIV and anti-cancer chemotherapeutic compound among other applications still under evaluation.

BACKGROUND TO THE INVENTION

Largely as a result of AIDS pandemic which is particularly evident in Africa, palliatives and/or cures have been sought by all research groups world wide. In Africa and more particularly in Zimbabwe, the Zimbabwe National Traditional Healers Association (ZINATHA) and local scientists have long believed that naturally occurring substances extracted from various medicinal plants have the required properties to the control and/or provide cures of HIV, cancers and other diseases.

To further their belief, ZINATHA entered into an agreement on Nov. 22, 1992 with the Developmental Therapeutics Program (DTP) Division of Cancer Treatment (DCT) of the National Cancer Institute (NCI) of the United States of America, whereby ZINATHA and NCI would collaborate in the evaluation of medicinal and other Zimbabwean plants and ZINATHA would supply to NCI such plant specimens and extracts as ZINATHA considered likely to have and/or contain active principles which could be extracted for structural elucidation and for clinical trials. Following upon this agreement, one Peter M. Mashava, (Ph.D.) of the University of Zimbabwe, undertook the task of investigating certain preferred specimens, notably *B. speciosus*. Using standard procedures, he isolated an active principle which he designated as "PMZ-1".

SUMMARY OF THE INVENTION

The invention relates to a method of treating cancer or HIV by administering an effective dosage of a dihydro-isoflavonone to a mammal infected with HIV or for treatment of symptoms of acquired immuno deficiency syndrome or cancer.

BRIEF DESCRIPTION OF THE DRAWINGS

FIG. 1 shows an isolation protocol of PMZ-1 from *Bolusanthus speciosus*.

FIG. 16 show a comparison of PMZ-1 to Nevirapine in an extended time course assay.

FIGS. 33a–33i are graphs showing dose-response curves for PMZ-1 derived by plotting PMZ versus $\log_{10}$ values of appropriate concentrations for each cell line.

DISCLOSURE OF THE INVENTION

Pre-extraction Sample Preparation

Figure 2:
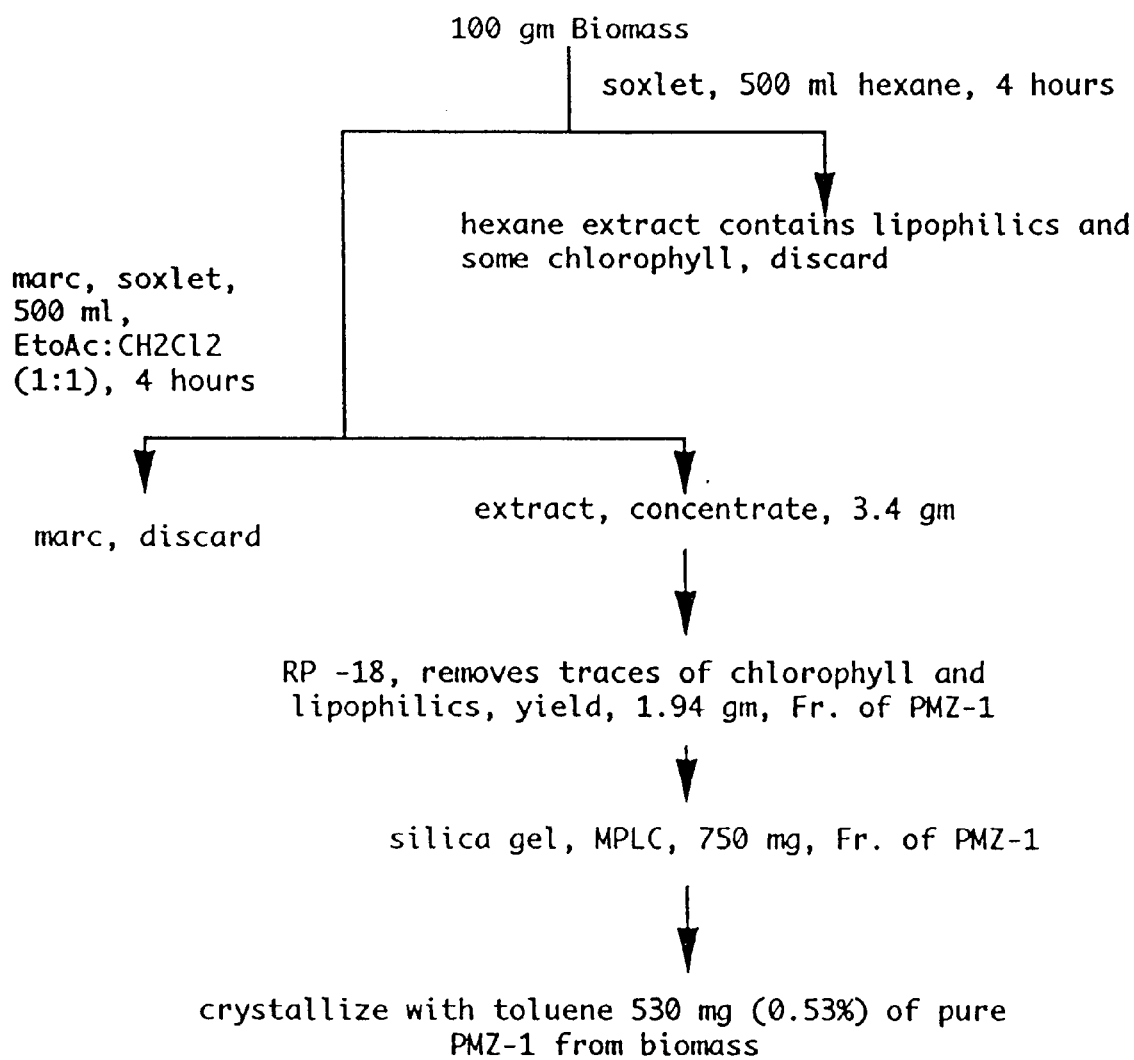
FIG. 2 is a flow chart showing isolation of PMZ-1 from stem bark of *Bolusanthus speciosus* Harms.

Wet stem bark of *Bolusanthus speciosus* was chopped in small pieces (≈1 inch). These were spread out on laboratory table to air dry for seven (7) days. Air dried stem bark was ground using a Retsch muhle grinder, model SK1 fitted with a five (5) mm sieve. Ground stem bark (250 gm) was placed into an percolaror/extractor, Kontes 100, 3000 ml size, to which a piece of cotton wool had been added to sieve as a filter. To the percolator/extractor, were added 1500 ml of solvent mixture; methylene chloride:methanol (4:1). This was left to soak overnight. Organic solubles were filtered through the cotton wool. The filtrate was evaporated at reduced pressure using a rotary eveporator with bath temperature maintained at 40° C. The crude extract was further dried under high vacuum (0.01 torr) to give 19.51 gm (7.8%) of the crude extract.

EXAMPLE 1

Isolation of PMZ-1

The crude extract (19.51 gm) was redissolved in 100 ml of methylene chloride:methanol (4:1) and 47 gm of silica gel 60 (0.040–0.063 mm, 230–400 mesh, EM Science); were added. The solvent was removed at reduced pressure at the rotary evaporator with bath temperature maintained at 40° C. and further dried under high vacuum (0.01 torr) to give silica gel coated extract. To a short column (Kontes 17×7 cm, ID, fitted with sintered glass of M porosity) was added silica gel up to 8 cm. The silica gel coated crude extract was added on top. The packed column was wetted with hexane (200 ml). The column was then eluted isocratically with toluene:ethyl acetate (9:1) collecting 20×100 ml fractions. Fractions 10 to 15 contained PMZ-1. These were combined and dried to give (7.86 gm) of impure PMZ-1 contaminated with chlorophyll from the stem bark. This sample (7.86 gm) was redissolved in methanol:methylene chloride (4:1) and 20 gm of reverse phase C-18 (Waters, part No. 20594, 55–105 microns, 125 Å or Alltech, 30–70 microns, 60 Å) were added. The mixture was dried at reduced pressure at the rotary evaporator followed by high vacuum drying (0.01 torr). The mixture was loaded on a flash column, as described before, containing 88 gm of C-18 silica gel. The column was wetted with methanol:water (1:1). A total of 100 ml of this solvent mixture was used and collected as single fraction. The column was then eluted with methanol:water (7:3)+3% v/v 2-propanol. A total of 9×200 ml fractions were collected. Fractions 3–6 containing impure PMZ-1 were combined and dried to afford 4.96 gm.

A sample of 3.87 gm of this material was coated with 30 gm of silica gel and fractionated by medium pressure liquid chromatography using Isco UA 6 UV/VIS detector fitted with type 11 optical unit. Solvent pumping was achieved by using Masterflex pump fitted with model 7090-62 pump head. Michel-Miller column (Ace glass cat. No. 5795-16, 350 mm), and solvent system, toluene:ethyl acetate (9:1) was used for the chromatographic separation. From this fractionation, 20×100 ml fractions were collected with the pump operating at 20–50 psi pressure. The desired semi-pure PMZ-1 was obtained in a single fraction 10, (3.30 gm) contaminated with traces of chlorophyll. Traces of chlorophyll were removed as described. Thus, the fraction 3.30 gm was redissolved in 50 mol of methanol to which 10 grams of C-18 was added. The solvent was removed at reduced pressure using a rotary evaporator with bath temperature maintained at 40° C. The C-18 coated compound was further dried at high vacuum (0.01 torr). The dried sample was added to Michel-Miller column (Ace glass, 5795-10, 300 mm) pre-packed with C-18. This was eluted with methanol:water (7:3)+3% v/v 2-propanol. The compound PMZ-1 (1.83 gm) was collected basically as as pure by TLC on C-18 plate developed with the same solvent above. Final purification was carried out by high pressure liquid chromatography, HPLC (Waters HPLC system; system controller 600 E, photodiode array detector 991; data retriever, NEC powermate SX plus; column, Waters RCM 25×10, millipore product). Both normal and reverse phase methods are suitable for the purification of PMZ-1. The conditions used are set out below, Tables 1 and 2, respectively. The reverse phase procedure was used as follows. The sample (1.80 gm) was dissolved in 1 ml methanol, A 100 μl aliquot was used per injection. A total of 11 injections, including washings, were used. The compound with a retention time of 12 minutes was collected and the solvent was removed at reduced pressure to afford 1.37 gm of pure PMZ-1.

TABLE 1

| Normal Phase Conditions: | |
|---|---|
| Solvent | toluene:ethyl acetate (9:1) |
| pressure | 1098–1104 psi |
| flow rate | 6 ml/minute |
| sample | 100 mg/injection |
| retention time | 8–9 minutes |
| UV-VIS detector | set at 290 nm |

TABLE 2

| Reverse Phase Conditions: | |
|---|---|
| solvent | methanol:water (7:3) + 3% v/v 2-propanol |
| pressure | 750–800 psi |
| flow rate | 7–8 ml/minute |
| sample | 100 mg/injection |
| retention time | 12 minutes; may be slightly different depending on conc. of sample injected and flow rate |
| UV-VIS detector | set at 290 nm |

Thin Layer Chromatography (TLC)

TLC plates were developed with methylene chloride:methanol (97:3). The spots on the plate are visible in short UV and are orange when sprayed with vanilin/sulphuric acid TLC spray reagent.

The summary of isolation is shown in the flow chart, FIG. 1. The yield of 1.37 gm would rationalize to 1.75 gm if all 4.96 gm were used for reverse phase chromatography step. The overall yield from the biomass would be 0.7%.

EXAMPLE 2

Isolation of PMZ-1

The dried stem bark (100 gm) was placed into a 400 ml soxlet to which a piece of cotton wool had been placed to serve as a filter. To a 1L round bottomed flask, 500 ml of hexane were added. Two to three boiling anti-bumping chips were also added. The sample was soxleted for 4 hours. This procedure removed most of the lipophillic compounds and most of the chlorophyll. The hexane extract was discarded. At the end of this period (4 hours), the receiver flask was replaced with one containing 500 ml of methylene chloride-:ethyl acetate (1:1). The sample was further soxleted for a further 4 hours. This step resulted in the extraction of PMZ-1 containing fraction. Completion of the extraction was monitored by collecting further fractions and testing for the presence of PMZ-1 by TLC on either normal silica gel or by reverse phase C-18 plates as described before. The solvent was removed at reduced pressure at the rotary evaporator with the bath temperature maintained at 40° C. The crude extract was further dried under high vacuum (0.01 torr) to afford 3.4 gm. This crude extract was coated on 10 gm of C-18 by the procedure of example 1. The coated material was flashed with 50 gm of C-18 using a solvent mixture methanol:water (6.5:3.5)+3% v/v 2-propanol/liter to afford 1.94 gm of semi-pure PMZ-1. This fraction (1.94 gm) was coated on 5 gm of silica gel and purified by MPLC using toluene:ethyl acetate (9:1) to afford 750 mg of semi-pure PMZ-1. This product was crystallized from toluene to give 530 mg (0.53% from biomass) colorless crystals of pure PMZ-1. The flow chart for example 2 is shown in FIG. 2.

EXAMPLE 3

Isolation of PMZ-1

A sample of crude extract (10 gm) was placed into a 500 ml round bottom flask and redissolved in methanol (100 ml). To this solution, 20 ml of water were added. The mixture was partitioned with 3×100 ml hexane. The hexane fractions were discarded. The aqueous methanol fraction was evaporated to remove as much of the methanol as possible. To the residual aqueous extract, was added a further 20 ml of water and partitioned with 3×100 ml of ethyl acetate. The combined organic layer was partitioned with 1×50 ml of brine. The organic layer was dried over anhydrous magnesium sulphate and evaporated to dryness at the rotary evaporator with bath temperature maintained at 40° C. This was followed by drying at high vacuum (0.01 torr). A fraction containing PMZ-1, 4.76 gm (46.76%) from crude extract was obtained. This fraction, 4.76 gm was redissolved in 30 ml of methanol assisted by a Cole-Parmer, model 08849-00 ultrasonic cleaner. Ten (10) grams of reverse phase C-18 were added. The solvent was removed at reduced pressure using a rotary evaporator with bath temperature maintained at 40° C. The C-18 coated compound was further dried at high vacuum (0.01 torr).

Figure 3:
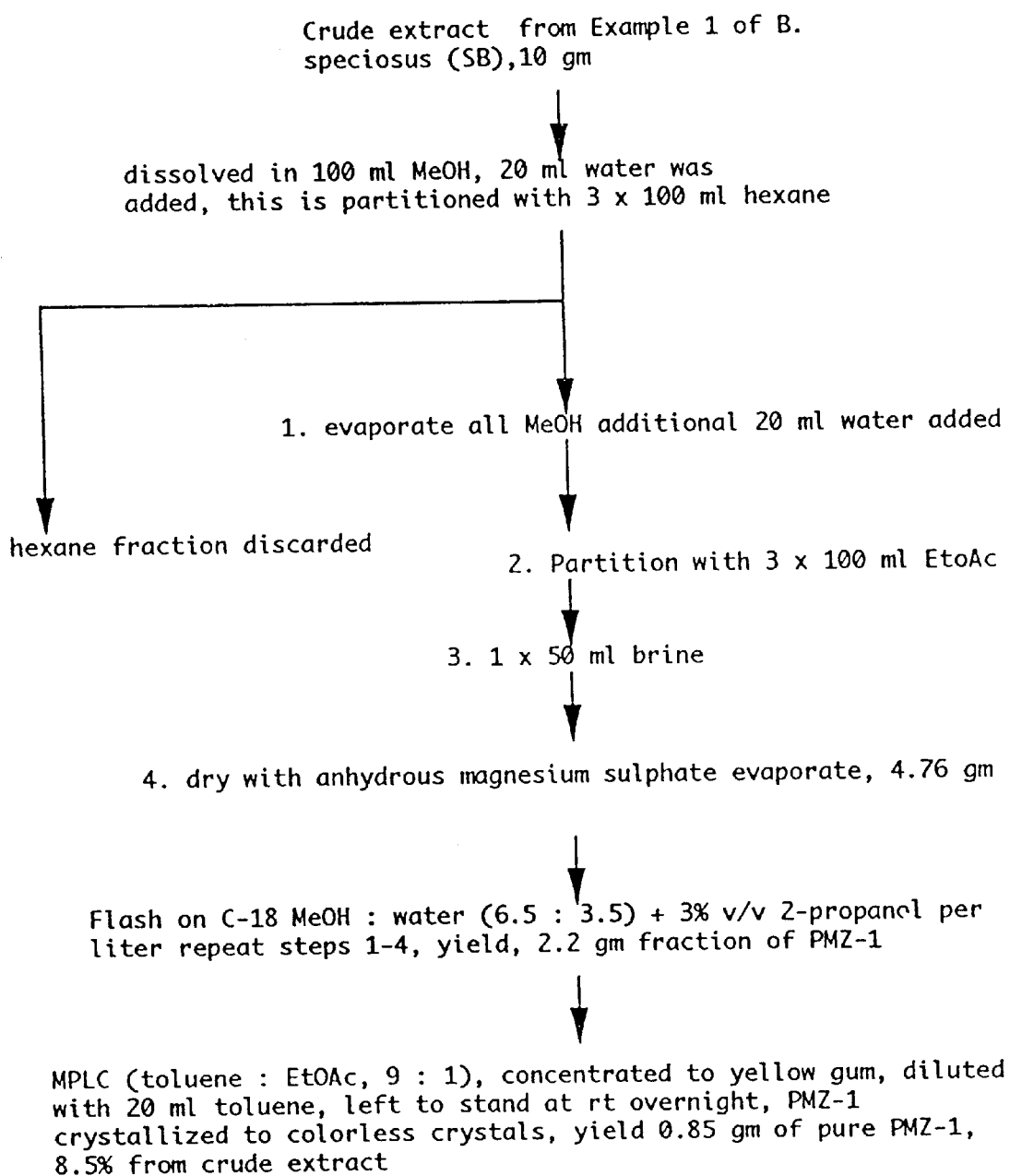
FIG. 3 is a flow chart showing isolation as pure PMZ-1 in 8.5% yield from crude extract of Example 1.

To a short column (Kontes 17×7 cm, ID, fitted with sintered glass of M porosity) was added C-18 silica gel up to 4 cm. The C-18 silica gel coated crude extract was added on top. The column was eluted with methanol:water (6.5:3.5)+3% v/v 2-propanol per liter. Ten (10)×50 ml fractions were collected. Fraction 5 contained impure PMZ-1, 2.2 gm. This was further purified by MPLC using toluene:ethyl acetate (9:1) followed by crystallization from toluene to afford 0.85 grams of pure PMZ-1 (8.5% yield from the crude extract). The flow chart of example 3 is shown in FIG. 3.

Crystallization of PMZ-1

A sample of pure PMZ-1 (140 mg) from HPLC purification was dissolved in toluene containing 1% ethyl acetate, with warming and the solution was allowed to stand at room temperature overnight. The colorless crystals of PMZ-1 were collected by filtration. Recrystallization was repeated three times. Crystals were dried, using a silicon oil bath, at 60–62° C. for 4 hours, 104° C. for four hours and at 120° C. overnight, under high vacuum (0.01 torr). The physical data is shown below. When hexane was added to the solution to slight cloudiness, white amorphous powder of PMZ-1 was obtained.

Physical Properties of PMZ-1 melting point: 139–140° C.

UV/Vis: lambda max=290 nm mass: $M^+$=370.1416; $^{13}C$ $M^+$=371.1405

FTIR(neat), $cm^{-1}$: 3366 (br), 2972 (s), 2932 (s), 1703 (s), 1641 (s), 1593(s)

Optical rotation 0° (96% ethanol, c=12.1 mg/m

NMR Structural Determination of PMZ-1 in $CDCl_3$/ $DMSOd_6$

The structure of PMZ-1 was determined using a sample (5.6 mg) in $CDCl_3$/$DMSOd_6$ (=120 µl) by one and two dimensional (1D and 2D) nuclear magnetic resonance (NMR) at 11.75 Tesla (500 MHz for $^1H$ and 125 MHz for $^{13}C$) at 27° C. The data were worked up on a Sparc II data station using standard VNMR1 software from Varian and an in-house sorftware. The mass spectra gave a mass of 370.1 ($C_{21}H_{22}O_6$ in agreement with the NMR finding of 21 carbons, 22 hydrogens, and 6 oxygens inferred from the proton and carbon chemical shifts.

The $^1H$ NMR analysis is given in Table 3 and gave the following key structural data. (1) Based on nOe volume comparison of H2'-5'Me=7.6 and H2'-4'Me=0.43, the assignments of 4Me and 5'Me could be reversed. (2) 3 exchangeable hydrogens at 12.16, 10.07 and 7.86 ppm correspond to an aromatic OH hydrogen bonded to a carbonyl, and two phenolic hydroxyls, respectively. (3) Two sets of meta coupled ($^3J$=2 Hz) aromatic doublets at 6.68, 5.56 and 6.00, 5.96 accounted for all of the aromatic protons. These data required two aromatic rings. The sets of protons were assigned based on the intensity skewing towards one another; and the dqcosy cross peaks. The J values were too close to use. (4) an ABX pattern at 4.53, 4.48, and 3.77 with a germinal J of 11.4 Hz and vicinal couplings of 5.0 and 7.9 Hz indicated an C- OMe group. (5) A OMe group at 3.77 (s) ppm integrated for 3 hydrogens. (6) A $CH_2CH$= coupled with a 7.2 Hz J showed long range Js to two =C—$CH_3$'s and indicated a $CH_2CH$=$C(CH_3)_2$, pentenyl group.

The $^{13}C$ NMR, Table 4, contained 21 peaks, and gave the following structural data. (1) One C=O at 195.81 ppm; (2) Nine quaternary aromatic carbons; five of which had chemical shifts indicating the attached oxygens; three indicating attached carbons and one indicating two ortho oxygens. (3) Five aromatic or double bonded carbons had protons attached, and four were assigned by heteronuclear multiple quantum coherence (hmqc) to be two sets of meta coupled protonated carbons: C2', C6' and C6, C8. The other CH= was assigned by hmqc to be part of the pentenyl group. (4) Six $sp^3$ carbons were found. The two carbons connected to the ABX confirmed the $OCH_2CH$ group. The 61.05 ppm peak was connected in the hmbc to the $OCH_3$ protons. The final three carbons connected to the $CH_2$ and two $CH_3$'s in the pentenyl group. Based on 12 ((2C+4-H)/2) sites of unsaturation, there are two aromatic rings containing all carbons, C=O, C=C not in the ring, and one other ring.

$^1$HNMR Data Table 3

| Assignment | Area | HMBC (8Hz) | Cosy | Delta (ppm) | Mult. (J Hz) |
|---|---|---|---|---|---|
| 5OH | 1 | C5, C6, C10 | — | 12.16 | s |
| OH | 1 | — | — | 10.07 | bs |
| OH | 1 | — | — | 7.86 | vbs |
| H2' | 1 | C3, C3's, C4', C6' | 6.56, 3.31s | 6.68 | d(0.4), d(2.3) |
| H6' | 1 | C3, C2', C4', C1* | 6.69 | 6.56 | d(0.6), d(2.2) |
| H6 | 1 | C5, C7, C8, C10 | 5.97 | 6.00 | ab(2.2) |
| H8 | 1 | C6, C7, C9, C10 | 6.00 | 5.96 | ab(2.1) |
| H2* | 1 | C5', C1*, 4*Me, 5*Me | 3.31, 1.71 | 5.24 | sept.(1.5), t(7.3) |
| H2eq | 1 | C3, C4, C9, C1' | 4.48, 3.77 | 4.53 | d(5.1), ab(11.4) |
| H2ax | 1 | C3, C4, C9, C1' | 4.53, 3.77 | 4.48 | d(7.9), ab(11.3) |
| H3 | 1 | C2, C4, C1', C2', C6' | 4.54, 4.48 | 3.77 | d(5.0), d(7.9) |
| 4'OMe | 3 | C4' | — | 3.77 | s |
| 1*CH$_2$ | 2 | C4', C5', C6', C2*, C3* | 5.24, 1.71 | 3.30 | d(7.2) |
| 5*Me* | 3 | C2*, C3*, 4*Me | 3.31 | 1.71 | q(1.3) |
| 4*Me* | 3 | C2*, C3*, 5*Me | — | 1.69 | d(1.0) |

*can be interchanged

NMR Data $^{13}$C Table 4

| Assignment | Area | Cluster | HMQC | Delta (ppm) | Mult. (J. Hz) |
|---|---|---|---|---|---|
| C4 | 1 | ‖ | — | 195.81 | s |
| C7 | 1 | ‖ | — | 166.71 | s |
| C5 | 1 | ‖ | — | 164.35 | s |
| C9 | 1 | ‖ | — | 162.74 | s |
| C3' | 1 | ‖ | — | 149.68 | s |
| C4' | 1 | ‖ | — | 144.94 | s |
| C5' | 1 | ‖ | — | 135.24 | s |
| C3* | 1 | ‖ | — | 132.10 | s |
| C1' | 1 | ‖ | — | 130.73 | s |
| C2* | 1 | ‖ | 5.24 | 122.39 | s |
| C6' | 1 | ‖ | 6.56 | 120.56 | s |
| C2' | 1 | ‖ | 6.68 | 114.01 | s |
| C10 | 1 | ‖ | — | 102.10 | s |
| C6 | 1 | ‖ | 6.00 | 96.47 | s |
| C8 | 1 | ‖ | 5.96 | 95.05 | s |
| C2 | 1 | | | 4.53, 4.48 | 70.97 | s |
| OMe | 1 | | | 3.77 | 60.12 | s |
| C3 | 1 | | | 3.77 | 50.46 | s |
| C1* | 1 | | | 3.30, 3.30 | 28.07 | s |
| 5*Me | 1 | | | 1.71 | 25.42 | s |
| 4*Me | 1 | | | 1.69 | 17.52 | s |

Figure 4:
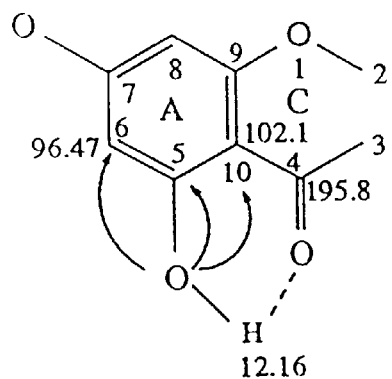
FIG. 4 through FIG. 7 show carbon types assembled from $^{13}C$ NMR data in which hmbc's completely describe the substitutions of the dihydro-isoflavonone, PMZ-1.
Figure 5:
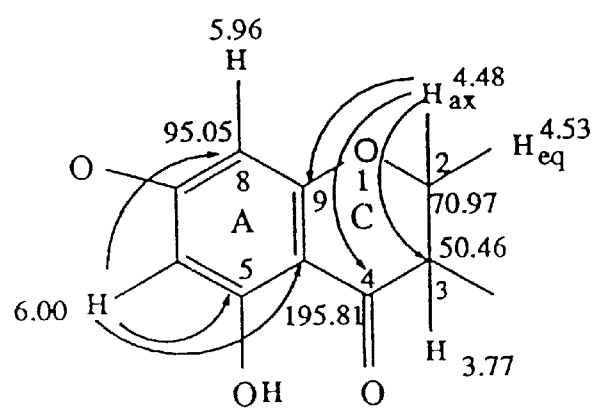
Figure 6:
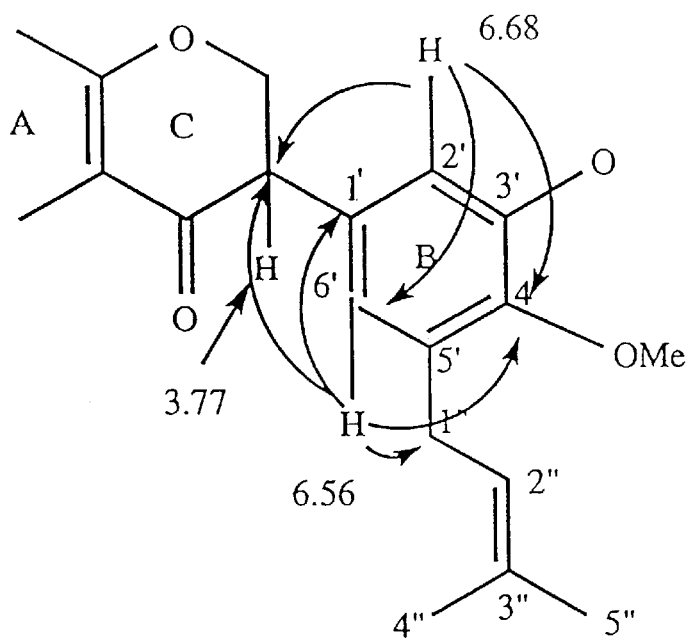
Figure 7:
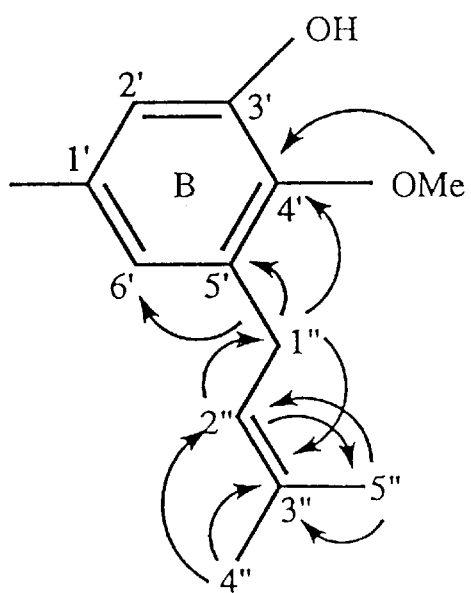

The carbon types were assembled using hmqc and the rings were assembled using the hmbc (heteronuclear multiple bond connectivity) experiment set for long range proton-carbon coupling of 8 Hz as follows. (1) Starting with one benzene ring with hydroxyl hydrogen bonded to an ortho carbonyl group as shown i FIG. 4. (2) Carbon 6, 96.47 with H6, 6.00, meta coupled to H8, 5.96, C8, 95.05 led to the following hmbc's as shown in FIG. 5. The ring closure from C2 to O1 was based on the chemical shift of C2, 70.97 ppm. (3) The hmbc's in FIG. 6 established the attachment of the final benzene ring. They also establish the position of the pentenyl group and the fact that the two oxygens are attached ortho to each other and next to the pentenyl group. They also confirm the C1–C3 bond. (4) The pentenyl group C1' to C5' has the following hmbc's shown in FIG. 7, which confirm not only its point of attachment but its sequence as well. The vicinal coupling constants of 7.2 Hz between H2' and H1' as well as long range J's between H2' and the methyl gropus at 4' and 5' are also in agreement. (5) The final piece of information involves the determination of the phenyl carbons, in ring B, to which OMe and OH groups are attached. This data are obtained from the hmbc's shown in FIG. 7. The OMe group is attached to the 4'C and OH group to the 3'C by the difference. These hmbc's completely and unequivocally describe the substitutions of the dihydro-isoflavonone, PMZ-1.

Figure 8A:
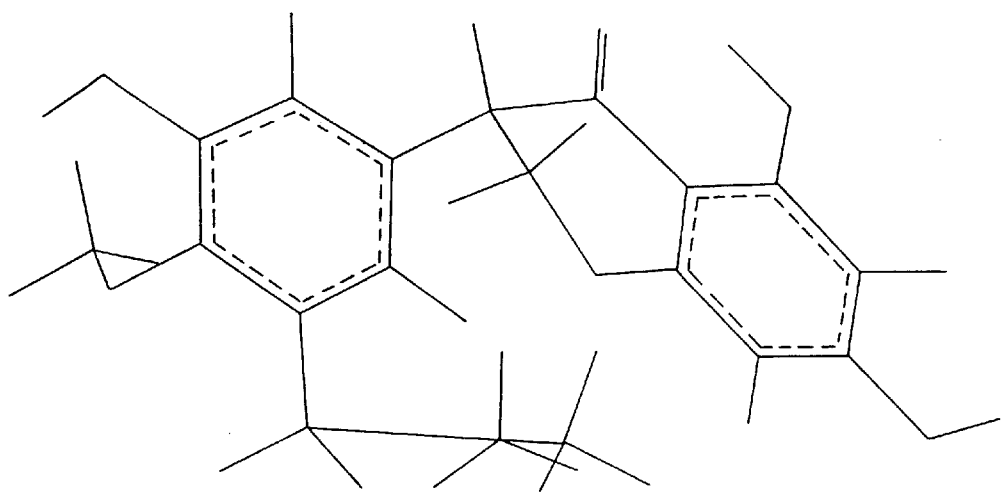
FIGS. 8a and 8b show configurations from a transverse Roesy experiment to confirm the structure and obtain additional data on the stereochemistry of PMZ-1.
Figure 8B:
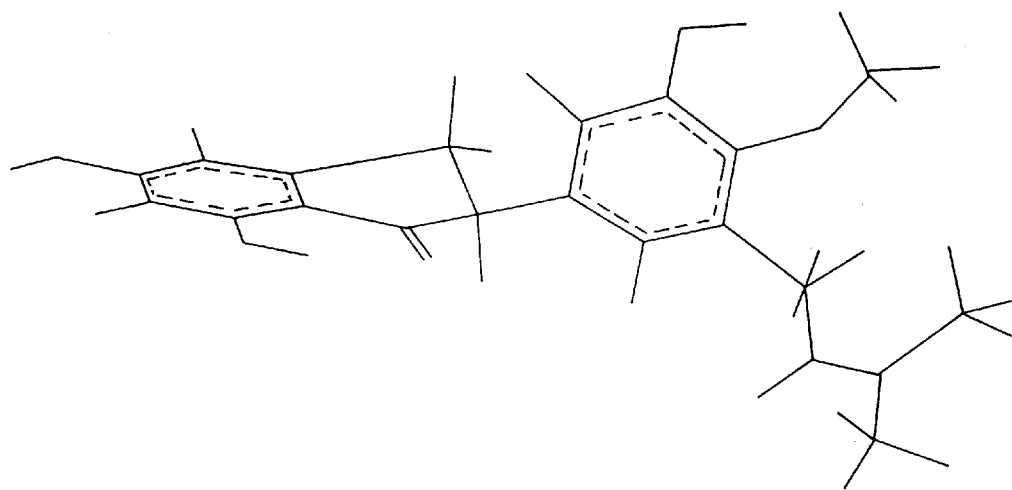

A transverse ROESY experiment was performed to confirm the structure and to obtain additional data on the stereochemistry of PMZ-1. The Tr ROESY data confirm that PMZ-1 has the 3' OH, 4'OMe and 5' pentenyl substitutions on B-ring. In addition, the stereochemistry in the vicinity of the C2 and C3 in the C-ring is tentatively assigned by using the volumes of the nOe crosspeaks in comparison to the energy minimized structures. The attachment of B-ring can be either pseudo-axial or pseudo-equatorial. FIGS. 8a and 8b. The nOe data suggest pseudo-axial attachment.

Figure 9:
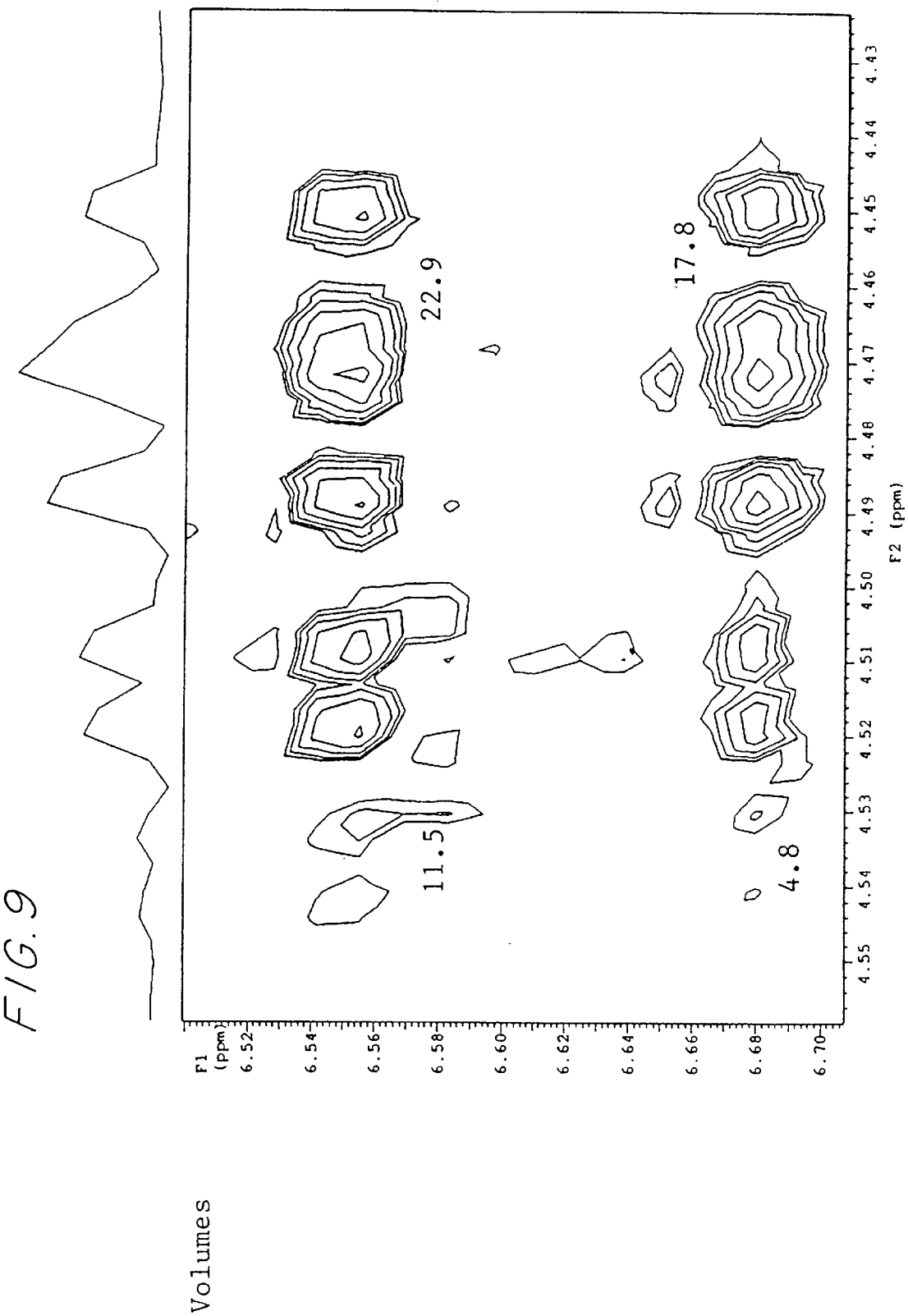
FIG. 9 shows the crosspeak volumes in the transverse Roesy.
Figure 10:
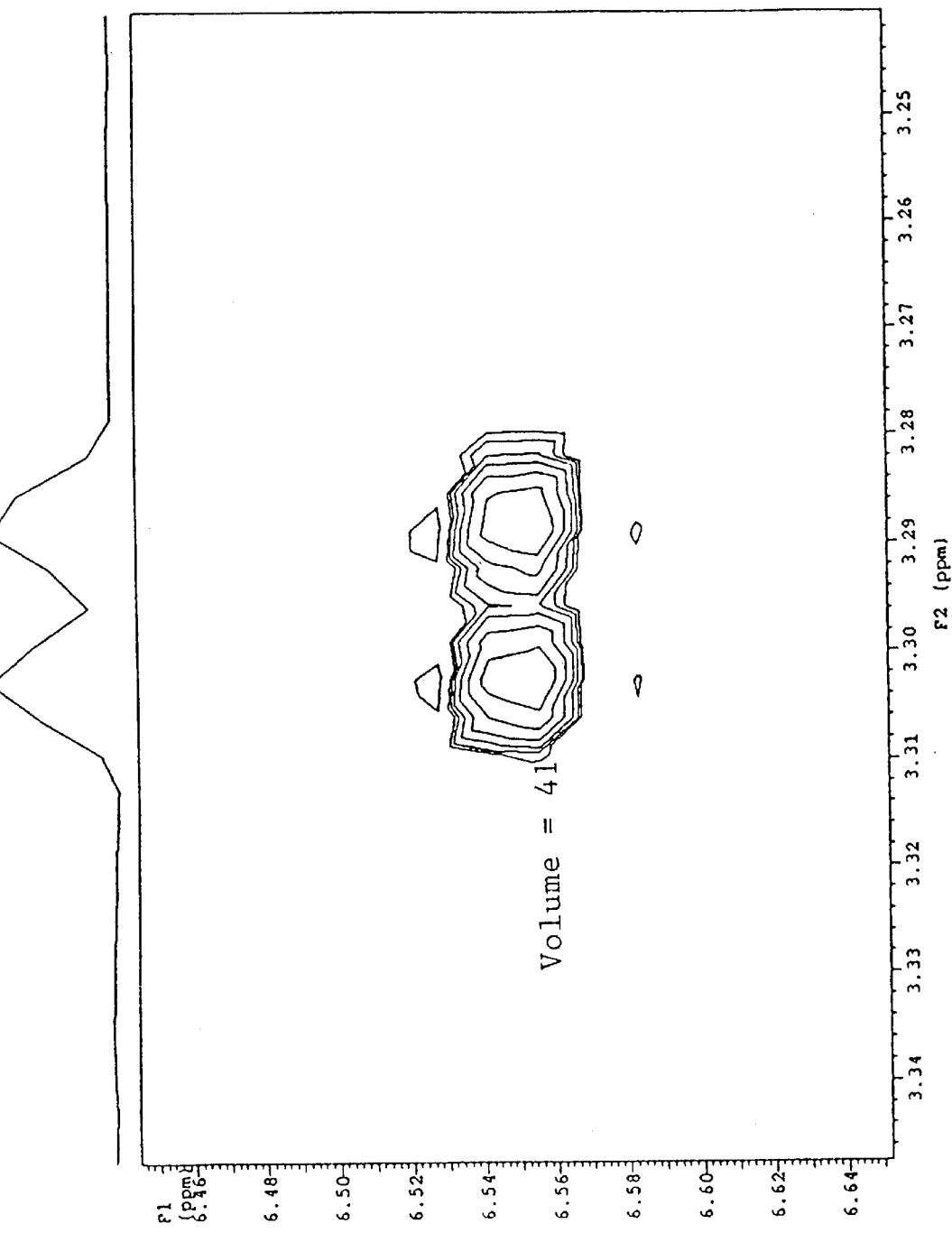
FIG. 10 shows the H6 to H1 crosspeak, which confirms the assignment of H6.
Figure 11:
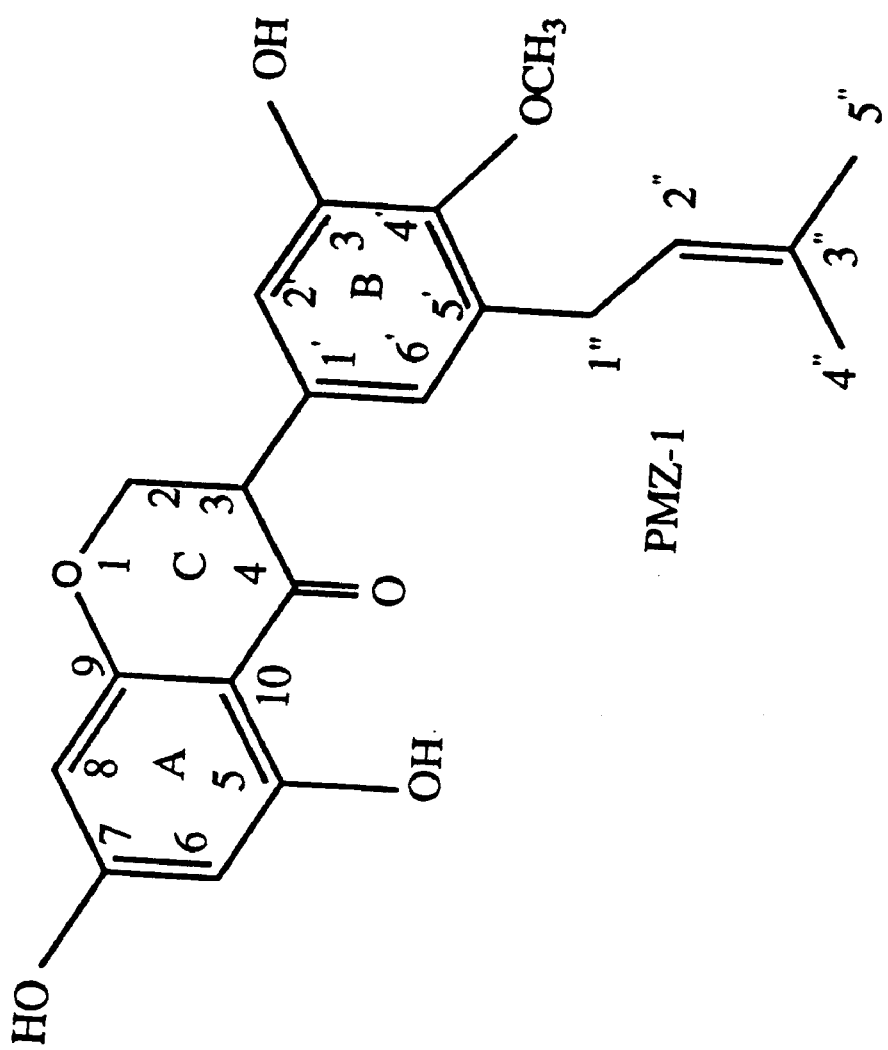
FIG. 11 shows a structure of PMZ-1 that is confirmed from nOe data and the hmbc's.

The energies of the discover energy minimized ring-B axial and ring-B equatorial were within 2 kcal of each other. With B-ring equatorial, the average distance from H2' to H2$_{ax}$ and from H2' to H2$_{eq}$ should be the same (FIG. 8b). With ring-B axial, the pseudo-equatorial H2 proton should, on the average, be closer to H2' and H6' than the pseudo-axial H2 proton (FIG. 8a). FIG. 9 shows that the crosspeak volumes in the Tr ROESY are larger for H2'-H2b and H6'-H2b than for H2'-H2a and H6'-H2a. Thus ring-B is axial and H2a is axial while H2b is equatorial. FIG. 10 shows the H6' to H1' crosspeak which confirms the assignment of H6'. Most significantly in the energy minimized structures, the axial attachment of the B-ring has H3 equi-distance between H2a and H2b. For the equatorial B-ring attachment, these distances are quite different. The nOe volumes experiment gives nearly identical volumes for PMZ-1, and for the H3-H2a and H3-H2b crosspeaks. The nOe data presented above and the hmbc's confirm the structure of PMZ-1 as shown in FIG. 11.

Two other compounds designated as 4382-39-1 (FIG. 12) and 4382-39-2 (FIG. 13) were also isolated along with PMZ-1. Both are devoid of HIV activity due to ability of pentenyl group at C8 (FIG. 12) or C5' (FIG. 13) to cyclize through the ortho OH groups at C7 or C4'. No further discussion will be done in this paper.

The data presented in this paper for the structural elucidation of PMZ-1 were compared with those presented in the published papers of Hostettmann et el. in *Planta Medica* (53, 1027, 1987; and ibid. 55, 282, 1989). It is clear that PMZ-1 is not the same compound as compound 1 described in these publications which has a m.p. of 58–59° C. and $(\alpha)_D$=4°. These values are different for 100% pure PMZ-1. A mixture of PMZ-1 and compound of FIG. 13 has m.p. of 59–60° C., in agreement with published compound 1. Compound 1 is a mixture of PMZ-1 and that shown in FIG. 13. A further review of the Chemical Abstracts indicated that our disclosure of the structure of PMZ-1 in this application is the first time that the structure of PMZ-1 has been completely described.

Applications of the Invention:

The compound, PMZ-1, has been shown to be active against various strains of HIV, active in some HIV mutants and against breast cancer. The search for effective chemotherapeutic compounds against the effects of the HIV virus has to be directed at the inhibition of the main viral enzymes responsible for its replication. The three major enzymes are reverse transcriptase, integrase and protease among other viral enzymes. The compound, PMZ-1, has been evaluated for its efficacy to inhibit various viral enzymes. The first point of replication of the virus in the host cells is initiated by the viral attachment and fusion with the $CD_4$ receptors on the surface of the host's helper T-lymphocytes (white blood cells). The virus uses its receptor glycoprotein to recognize the $CD_4$ of the host lymphocites. This attachment is then followed by the fusion of the viral and cellular membranes. At this stage the virus is able to penetrate the host cell. Once the virus is within the cell, it uses its reverse transcriptase enzyme to copy the double stranded DNA of the viral RNA genome. This process is followed by integration of the double stranded DNA of the virus into the chromosomes of the host nucleus, a process catalyzed by the integrase enzyme. The protease enzyme is initially used to cleave the integrase from the reverse transcriptase enzyme. Thus the availability of the integrase enzyme to perform its functions independently is made possible by the protease enzyme.

An effective inhibition of any or all of these major viral enzymes by any chemotherapeutic agent would be an important stage towards the eradication of the HIV/AIDS virus. The results of the tests using PMZ-1 as a potential chemotherapeutic compound against the HIV virus are described below.

Figure 14:
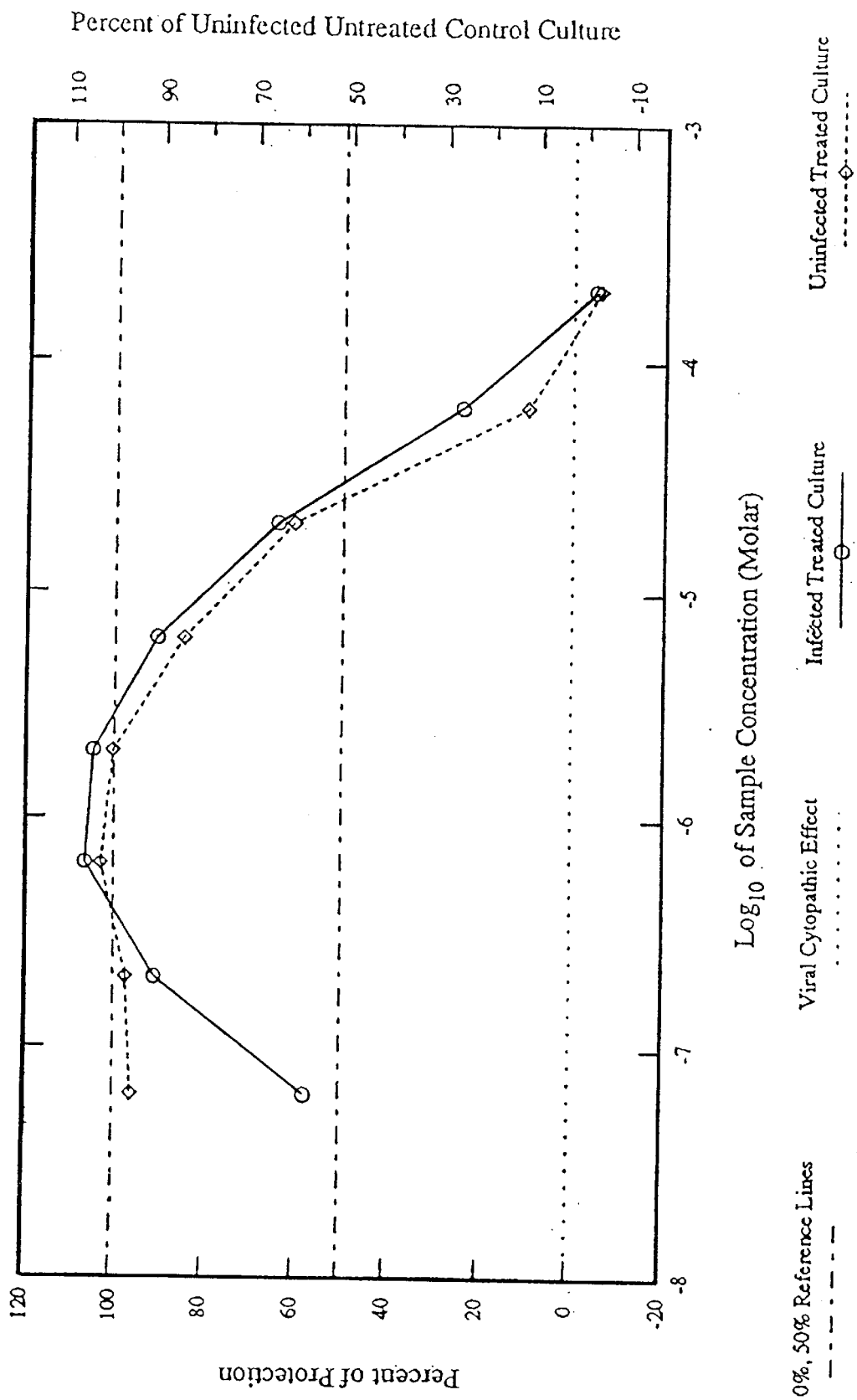
FIG. 14 is a graph showing in vitro activities for PMZ-1 that provides the results summarized in TABLE 5.

Anti-HIV Screens Using PMZ-1:

The compound (PMZ-1) was evaluated at the National Cancer Institute (NCI) of the United States' in vitro anti-AIDS Drug Discovery Program (Weislow, O. W. et al. *J. Natl. Cancer Inst.*, 81:577–586, 1989). The compound showed good protection of the CEM-SS when assayed for HIV-$1_{RF}$ and the results are shown in FIG. 14. The data presented in FIG. 14 is divided into three sections:

1. Sample and Test Identification Section:

The section specifies the sample tested by its NSC #D-675740-J along with the compound code name (COMI: PMZ-1), the actual experimental number from which the results were recorded (Plate), the laboratory which performed the experiment (Lab), the date of the experiment (Test date), the date the report was printed (Report date), and the cell line used in the test (Cell line). The solvent used in formulating the compound for testing is indicated (Solvent). The SSPL and Solubility Ind. are used for administrative purposes.

2. Graphics Results Summary Section:

This section displays a plot of the $\log_{10}$ of PMZ-1 in molar concentrations against the measured test values expressed as a percentage of the uninfected, untreated control values. The solid line represent the percentage of surviving HIV-infected cells treated with PMZ-1, at various concentrations, relative to uninfected, untreated controls. This line expresses the in vitro anti-HIV activity of PMZ-1. The dashed line depicts the percentage of surviving uninfected cells treated with PMZ-1 relative to the same uninfected, untreated controls. This line represent the in vitro growth inhibitory properties of PMZ-1. The dotted reference line represent the viral cytopathic effect. The line shows the extent of destruction of cells by the virus in the absence of treatment and is used as a quality control parameter. The survival values of this parameter less than 50% are considered acceptable in this protocol. The percent of protection has been calculated from the data and is presented on the left side of the graph.

3. Tabular Dose Response Data and Status:

This section provides a listing of the numerical data plotted in the graphics section. The approximate values for 50% effective concentration ($EC_{50}$) against HIV cytopathic effects, 50% inhibitory concentration ($IC_{50}$) for cell growth, and Therapeutic Index (TI=$IC_{50}/EC_{50}$) have been calculated for each test and are provided The NCI staff determination of the activity of PMZ-1 is printed in the lower left-hand corner.

TABLE 5

| Virus Strain | $EC_{50}(M)$ | $IC_{50}(M)$ | TI |
|---|---|---|---|
| HIV-$1_{RF}$ | $1.1 \times 10^{-7}$ | $2.0 \times 10^{-5}$ | 181 |
| HIV-$1_{1118}$ | $5.8 \times 10^{-8}$ | $4.6 \times 10^{-5}$ | 793 |
| HIV-1 AZT$^{res}$ | $1.6 \times 10^{-7}$ | $4.2 \times 10^{-5}$ | 263 |
| HIV-1 AZT$^{sen}$ | $1.3 \times 10^{-7}$ | $3.5 \times 10^{-5}$ | 269 |
| HIV-1 $_{A17}$ | $4.2 \times 10^{-6}$ | $3.8 \times 10^{-5}$ | 9.0 |
| HIV-1 $_{N119}$ | $2.3 \times 10^{-5}$ (W) | $6.0 \times 10^{-5}$ | 2.6 |
| HIV-1 $_{DPS}$ | $9.8 \times 10^{-7}$ | $4.2 \times 10^{-5}$ | 49 |
| HIV-1 $_{ROD}$ | W | $2.8 \times 10^{-5}$ | — |
| SIV $_{MAC}$ | W | $3.5 \times 10^{-5}$ | — |
| Mono/MAC's | $2.0 \times 10^{-7}$ | $>2.0 \times 10^{-4}$ | $>1.269$ |
| PMBC's | $6.0 \times 10^{-7}$ ($IC_{50}$) | $4.8 \times 10^{-5}$ | 80 |

The compound PMZ-1 was also tested in a range of in vitro activities and the results are summarized in Table 5. The compound showed greatest therapeutic index (TI) against Mono/Mac resistant strain.

Figure 15:
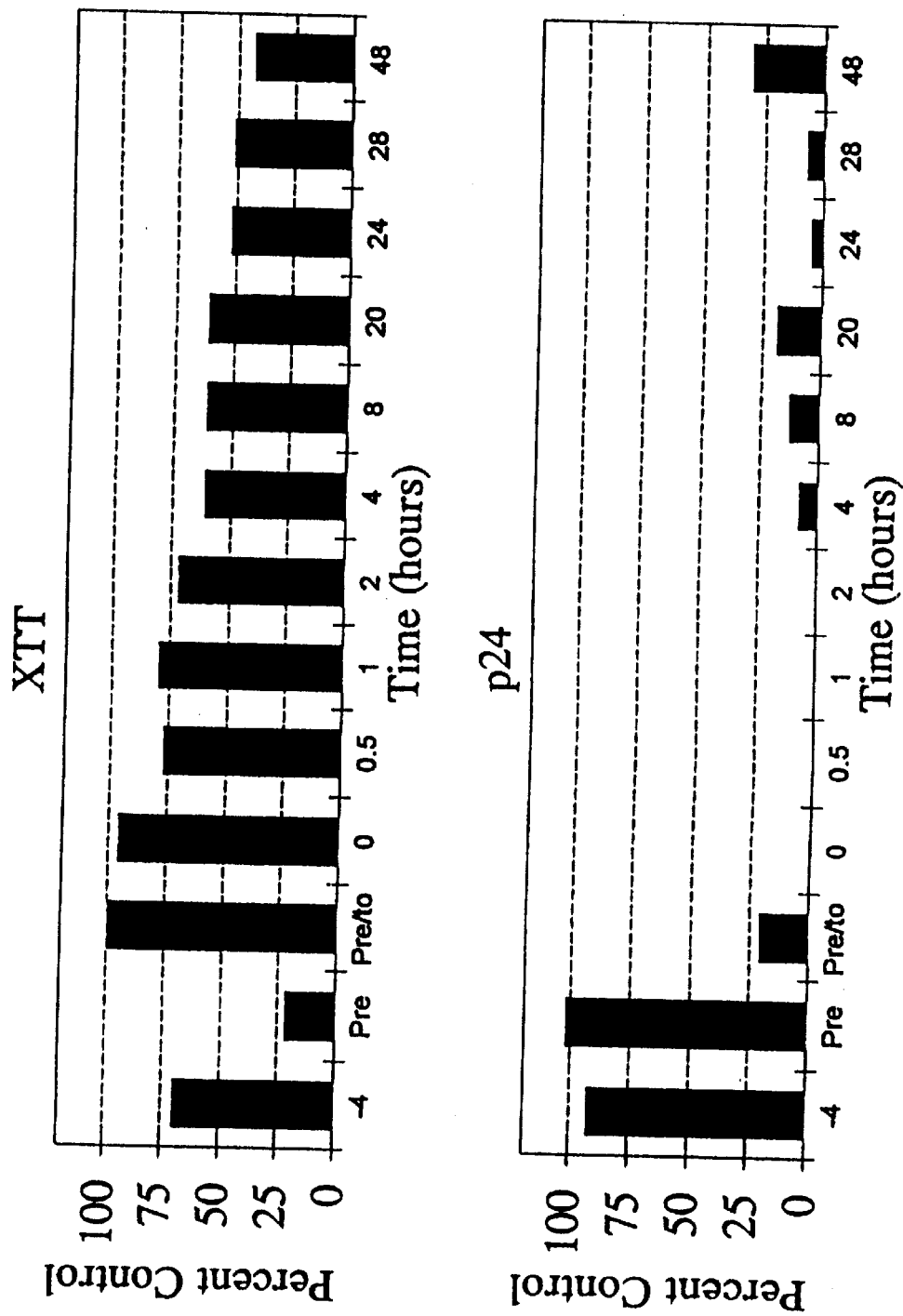
FIG. 15 shows the effects of PMZ-1 on p24 and XTT in a time course assay.

Time Course Experiments:

In order to identify the stage(s) of HIV replication that is affected, the compounds were evaluated in a high multiplicity of infection (MOI) acute phase time-of-addition assay (TOA) (Cushman et al., 1994). CEM-SS cells ($1 \times 10^5$) were pre-incubated with HIV-$1_{IIIB}$ (MOI=1.0) at 0–4° C. for 1 hour to allow attachment of the virus to the cells but not fusion. Samples were then washed three times with ice-cold media to remove unbound virus. The samples were then rapidly warmed to 37° C. (at time zero, $t_o$), allowing the infectious cycle to proceed. The compound (1 μM of PMZ-1) was included during the preincubation step only (pre), or during the preincubation step and the added back to $t_o$ (Pre/$t_o$) following the removal of residual virus or added to samples only at $t_o$ or at various times after warming at 37° C. (t=0.5, 1, 2, or 4 hours post-warming). Dextran sulfate (100 μg/ml and 2',3'-dideoxycytidine (ddC) (10 μM) served as controls for inhibitors of virus attachment and reverse transcriptase, respectively. After 24 hours of incubation, the cells were collected by centrifugation, lysed in QuickLyse buffer (10 mM Tris, pH 8.3, 50 mM KCl, 2.5 mM $MgCl_2$, 0.1 mg/ml gelatin, 0.45% Nonidet P-40, 0.45% Tween-20 containing 100 μg/ml proteinase K, incubated at 56° C. for two hours and boiled for 20 minutes. The products of viral transcriptase were amplified by polymerase chain reaction (PCR) using LTR/gag primer pairs (M667/M661, Recombinant DNA Laboratory, Program Resources, Inc. NCI-FCRDC, Frederick, Md., USA) and products of the β-globin gene were amplified using primer pairs as previously described (Zack et al., *Cell*, 61, 213–22, 1990). Amplified products were analyzed by electrophoresis in 2% agarose gels and visualized by ethidium bromide staining. The specificity of the products were verified by restriction enzyme cleavage and by Southern blot hybridization. The results of these tests are summarized in FIG. 15.

When PMZ-1 is compared with another non-nucleoside HIV inhibitor, Nevirapine, PMZ-1 offers cell protection for more than 48 hours after administration of the drug. The comparative studies are shown in FIG. 16. The activity was measured by the production of p24 protein.

Figure 17:
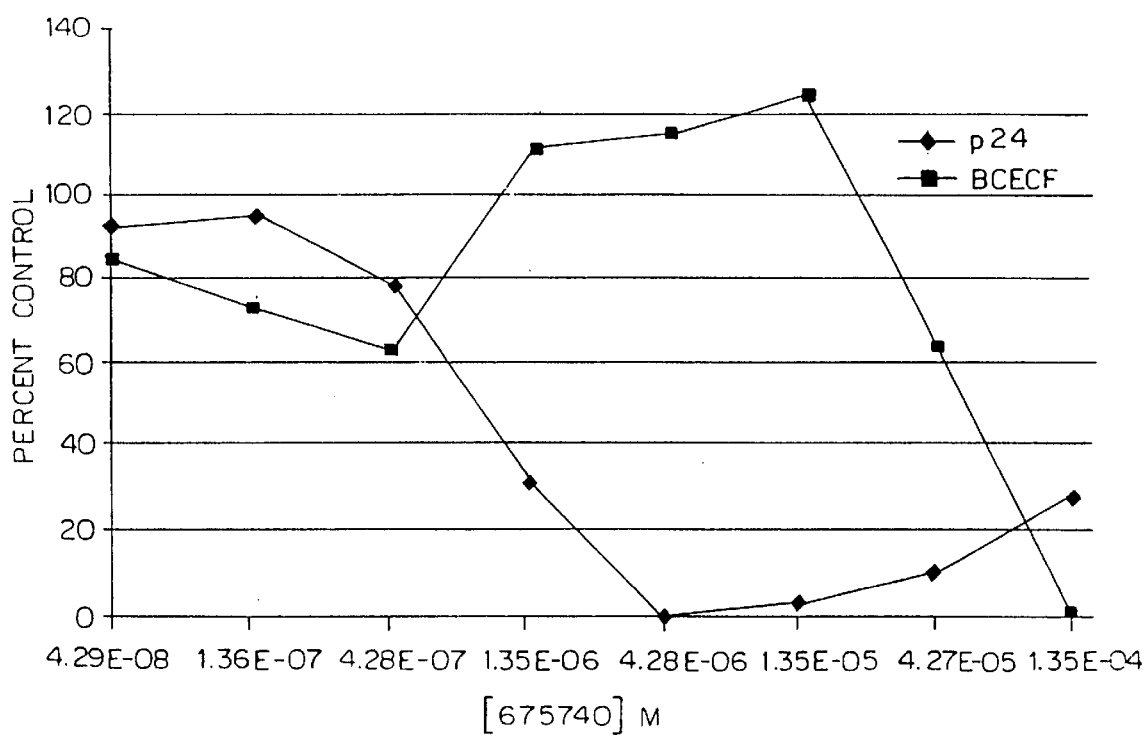
FIG. 17 shows a graph of a virus attachment and fusion assay utilized by the p24 antigen-capture assay.
Figure 18:
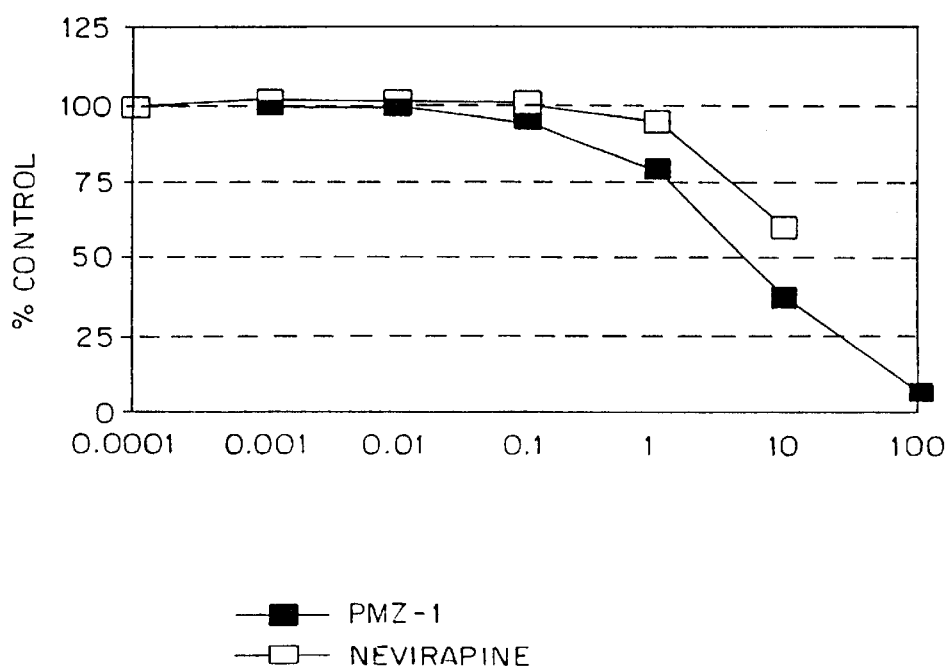
FIG. 18 shows a graph of a radioactive RT inhibition assay using r(A):d(T) as a template.
Figure 19:
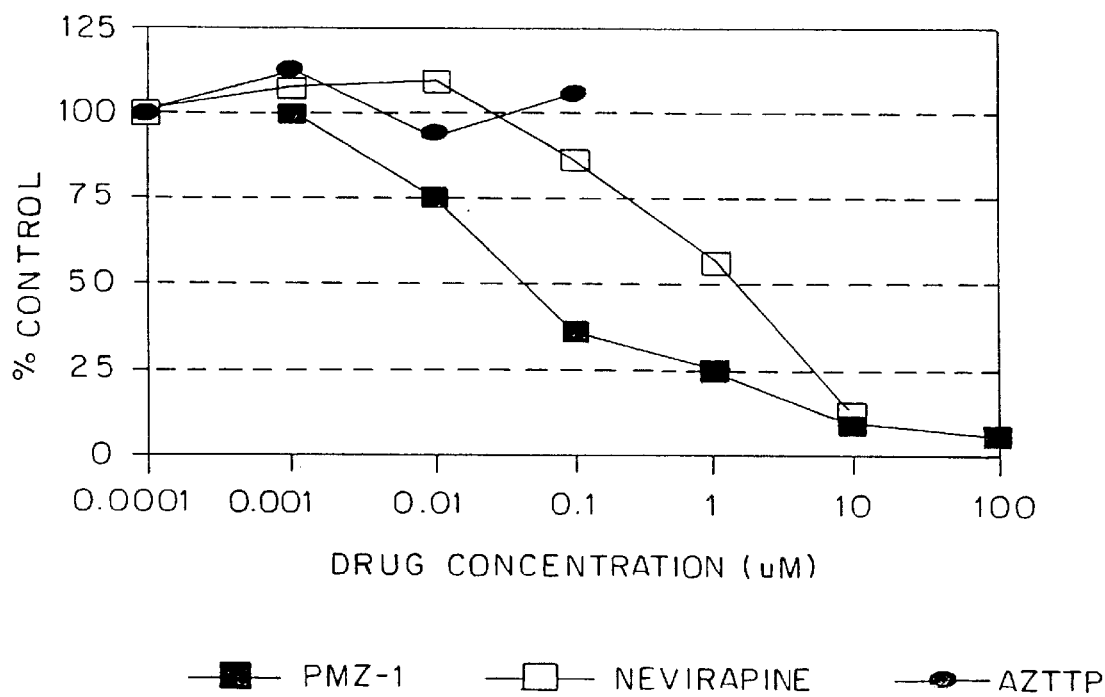
FIG. 19 shows a graph of a radioactive RT inhibition assay using r(C):d(G) as a template.
Figure 20:
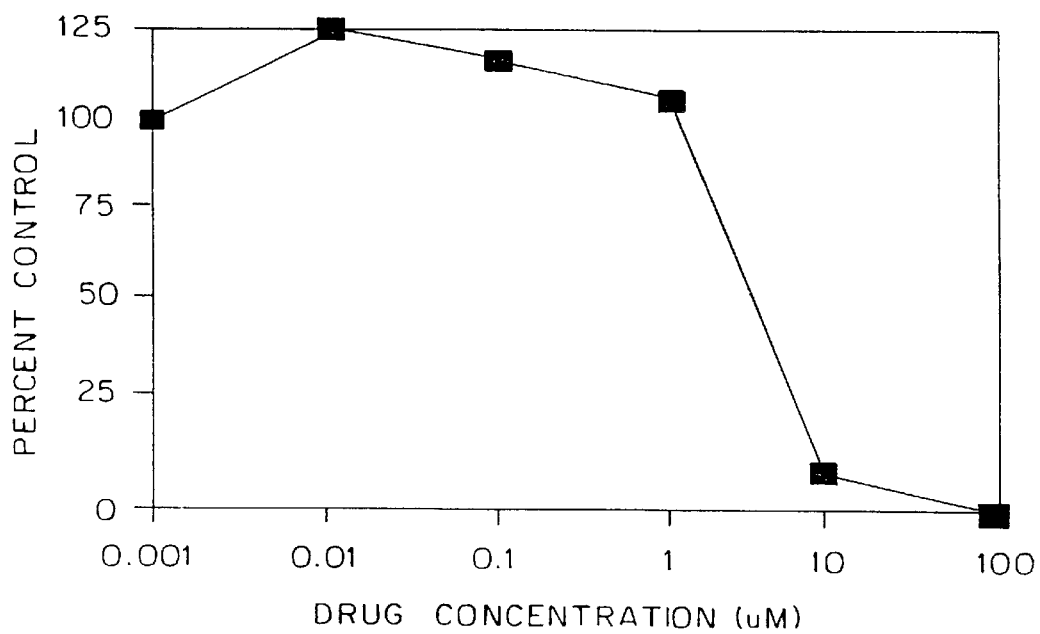
FIG. 20 shows a graph of the effect of PMZ-1 675740 on HIV-1 protease activity.

Virus attachment and fusion Assay:

Binding of HIV-$1_{RF}$ to fresh peripheral blood mononuclear cells (PBMC's) was measured by a p24 based assay (Rice et al., *PROC. NATL. ACAD. Sci. USA*, 90, 9721–9724, 1993). Briefly, 5×10⁵ PBMC's were incubated with a concentrated stock of virus for 30 minutes at 37° C. The unbound virus was washed away and the cell associated virus was solubilized in 1% Triton X-100, 1% bovine serum albumin (BSA) and analyzed by the p24 antigen-capture assay as described above. The results are shown graphically in FIG. 17.

Binding and Enzymatic Assay:

The binding of gp120 to $CD_4$ was analyzed using an antigen-capture enzyme-linked immonosorbent assay (ELISA) from DuPont. All steps off the assay were carried out according to the manufacturer's protocols. The effect of the drugs on the in vitro activity recombinant reverse transcriptase (RT) was determined by a previously described method (Buckeit and Swanstron, *AIDS RES HUMAN RETROVIRUSES*, 7, 295–302, 1991). The assay measures the incorporation of ($^3$H)-TTP to the artificial poly (rA): oligo (dT) or poly (rC): oligo (dG) homopolymer primer/template. Samples (5 μl) were blotted to DE81 paper, washed extensively with 5% dibasic sodium phosphate and then quantified on a Packard Matrix 9600 Direct Beta Counter. The compound 3'-Azido-3'deoxythymidine-5'-triphosphate served as a positive control for the inhibition for RT; and the absence of RT served as negative control.

Figure 21:
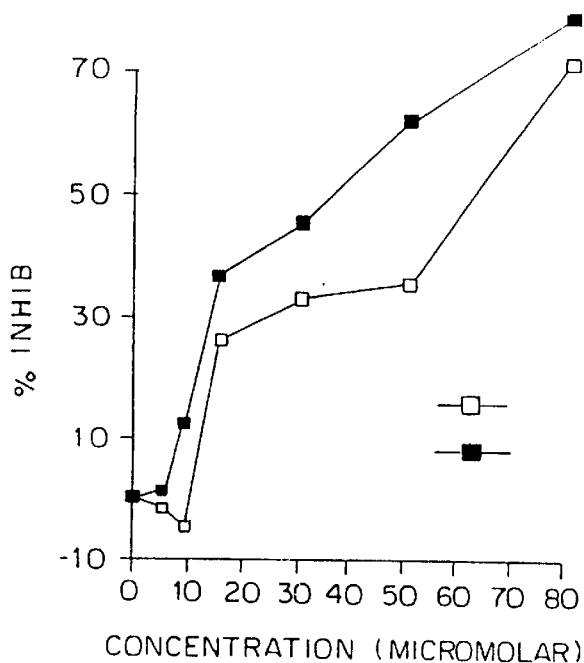
FIG. 21 is a graph showing the results of integrase activity.
Figure 22:
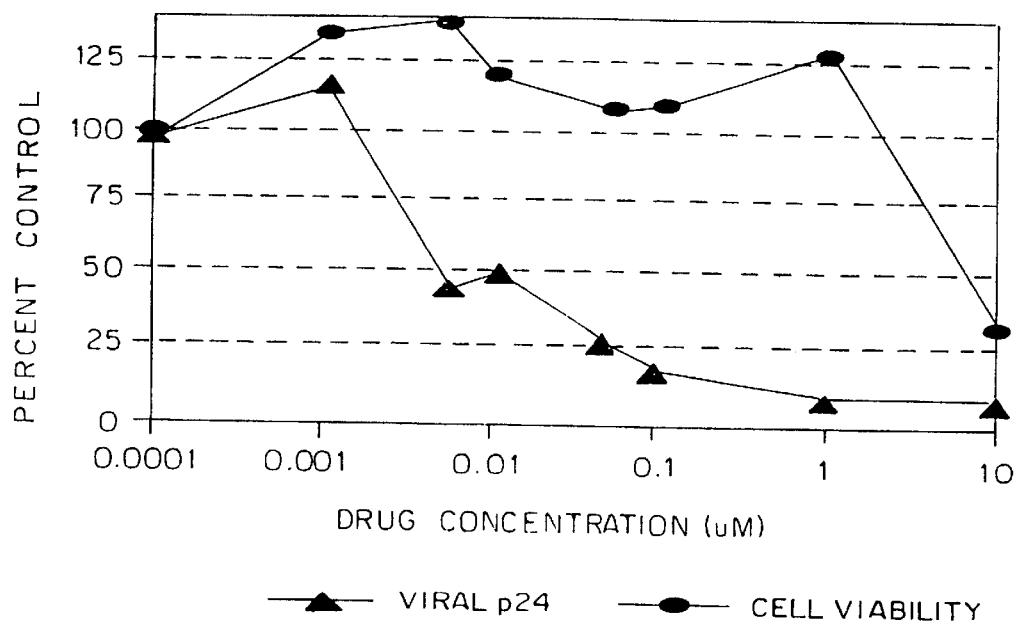
FIG. 22 is a graph showing inhibition of HIZ-1 Ada infection of human MO/MO cultures by PMZ-1.

Protease Activity:

The HIV protease activity was quantified by a reverse-phase HPLC assay utilizing the Ala-Ser-Glu-Asn-Tyr-Pro-Ile-Val-Amide substrate (Multiple Peptide Systems, San Diego, Calif.) as described (E. M. Wondrak et al., *FEBS LETT*, 280, 347–350, 1991). The results are shown in FIG. 21. The results of integrase activity are shown in FIG. 21.

Figure 23:
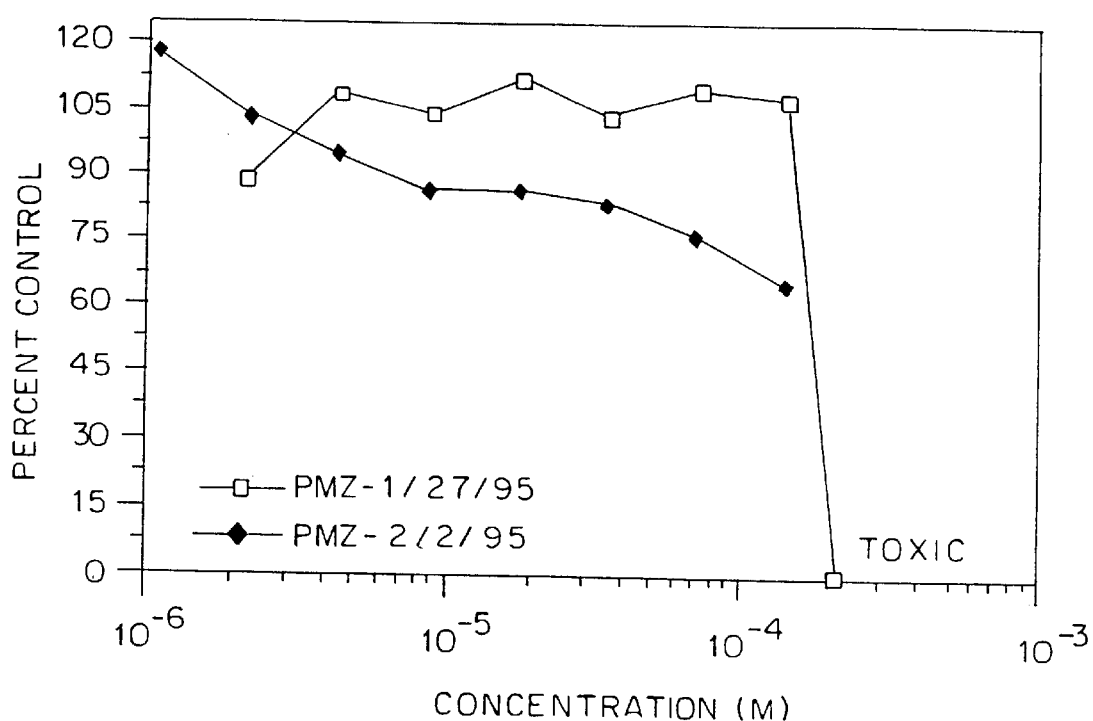
FIG. 23 is a graph showing that PMZ-1 has no effect on the attachment of virons on the cell receptors nor effect on the fusion of virons with the cells containing $CD_4$ receptors with those expressing viral envelope glycoproteins.
Figure 24:
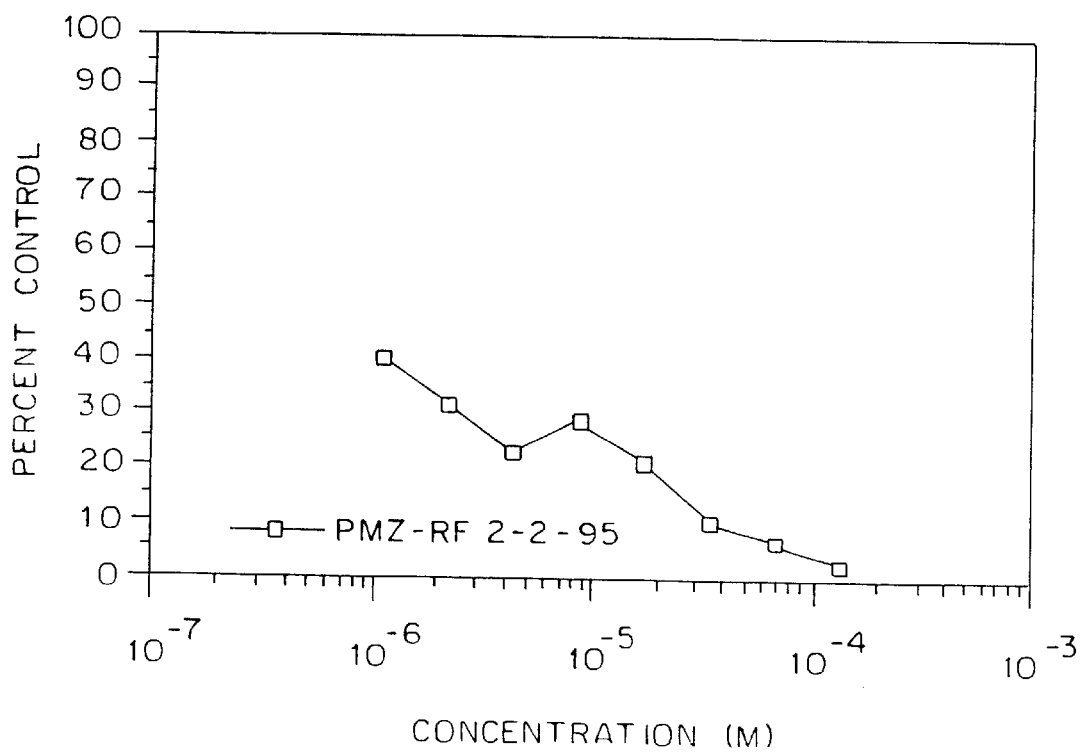
FIG. 24 is a graph showing the results for independent syncytia response for PMZ-1 on Magi cells.
Figure 25A:
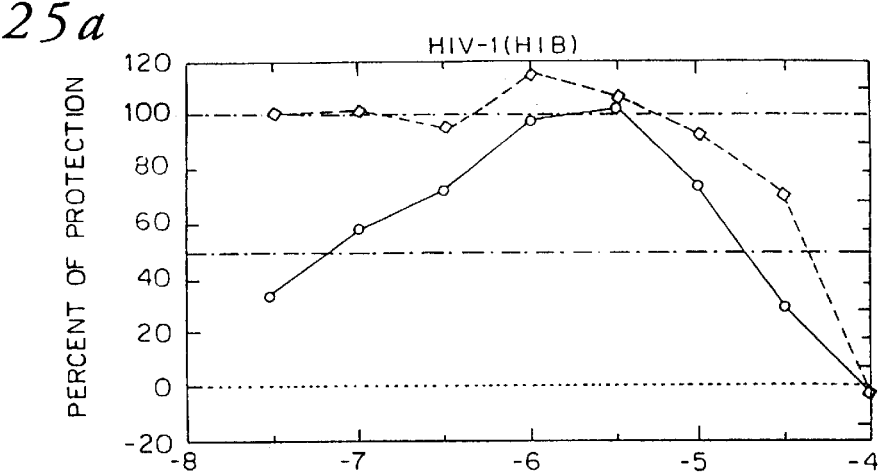
FIGS. 25a–25f are graphs showing PMZ-1 activities against various mutants shown in TABLE 6.
Figure 25B:
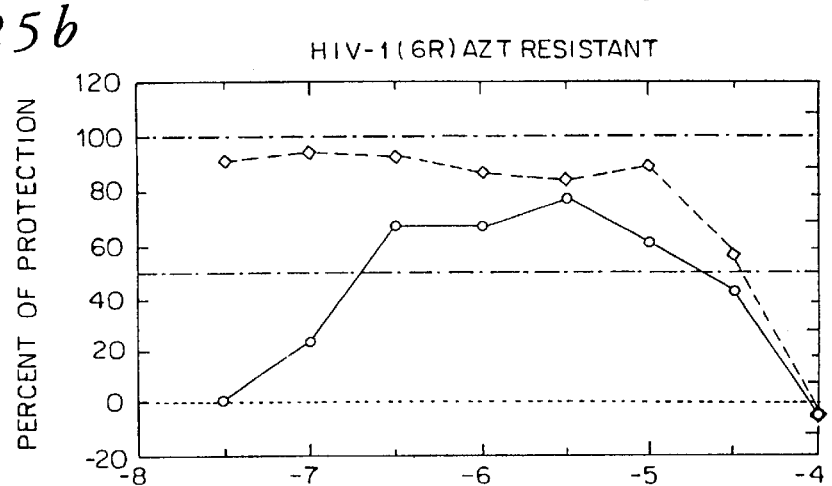
Figure 25C:
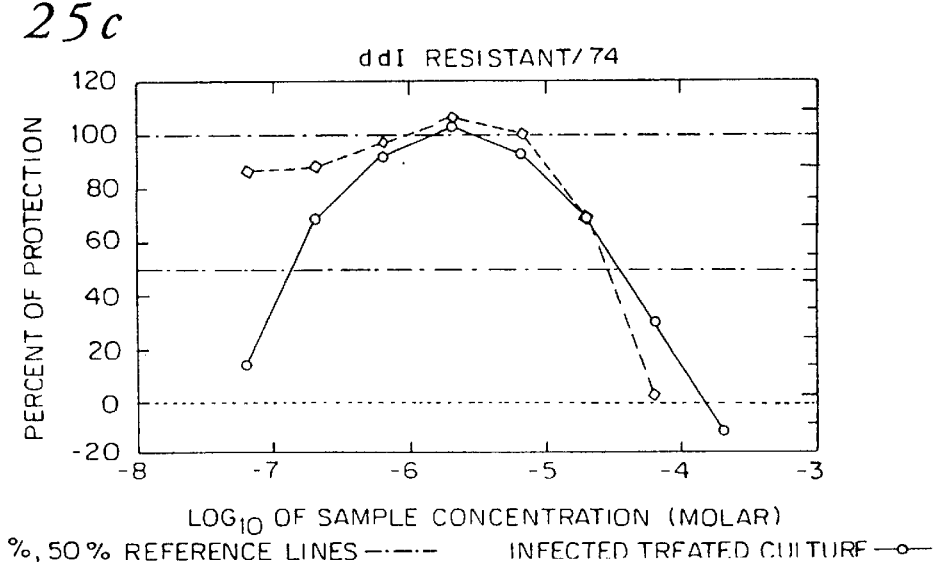
Figure 25D:
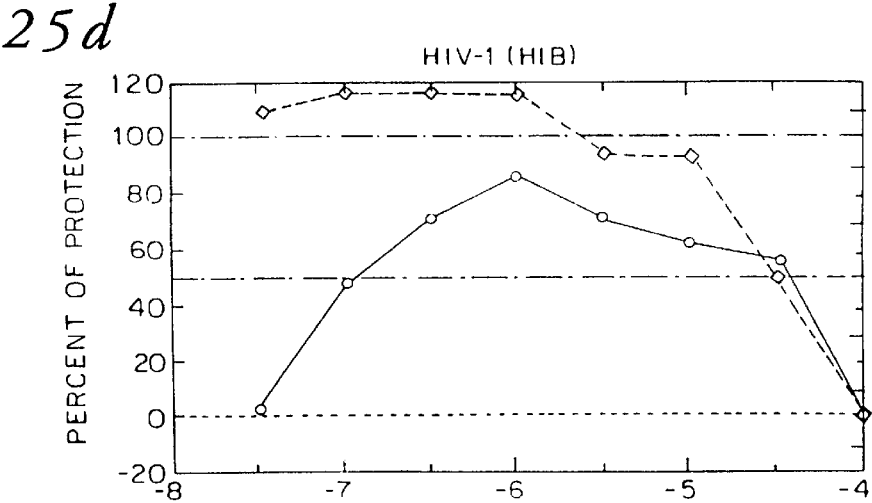
Figure 25E:
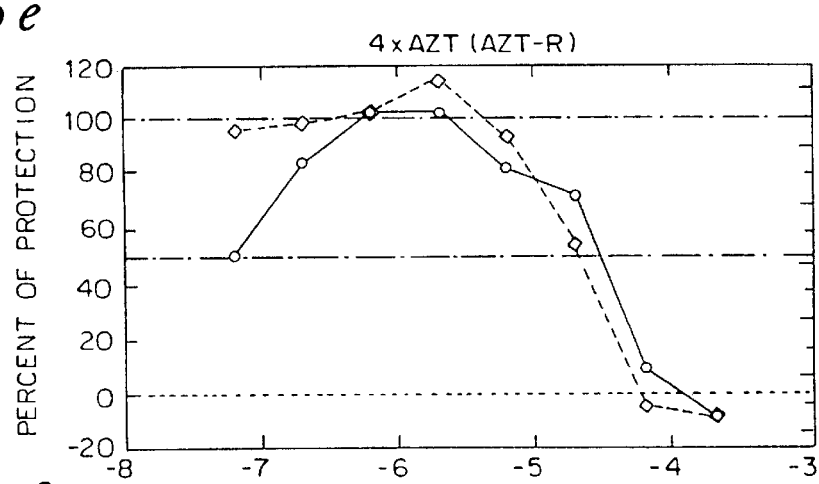
Figure 25F:
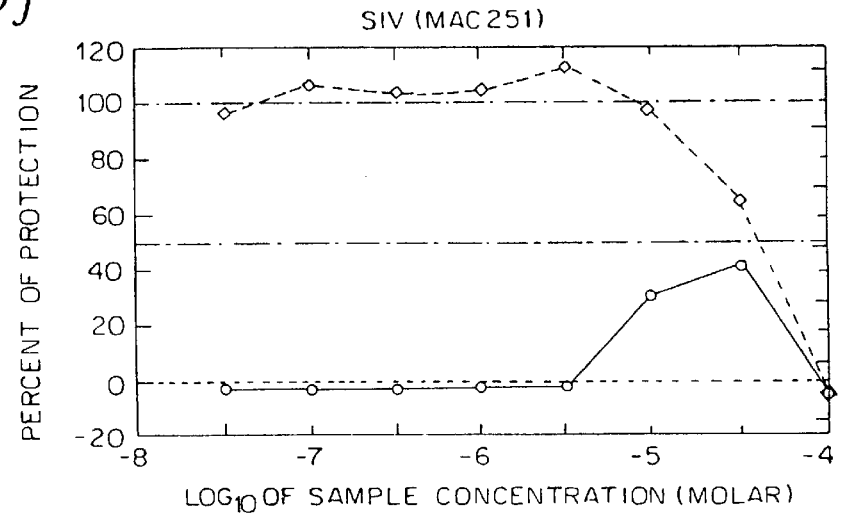
Figure 26A:
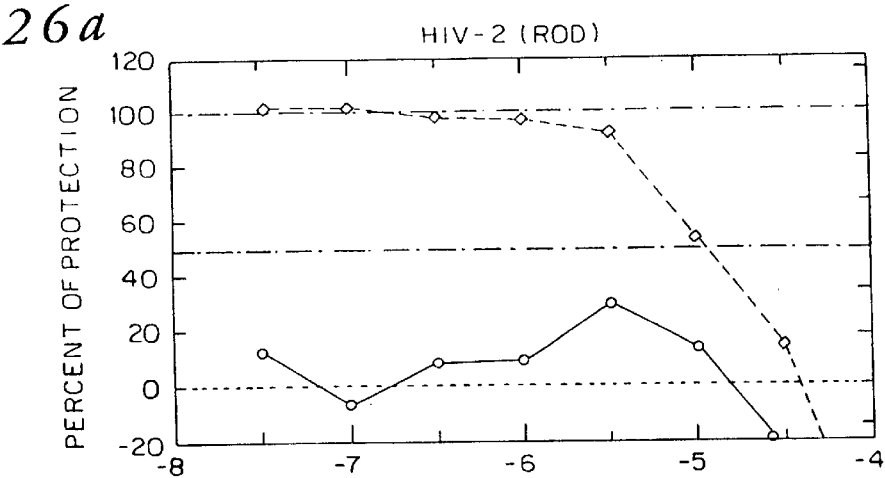
FIGS. 26-a–26-f are graphs showing PMZ-1 activities against various HIV mutants as shown in TABLE 6.
Figure 26B:
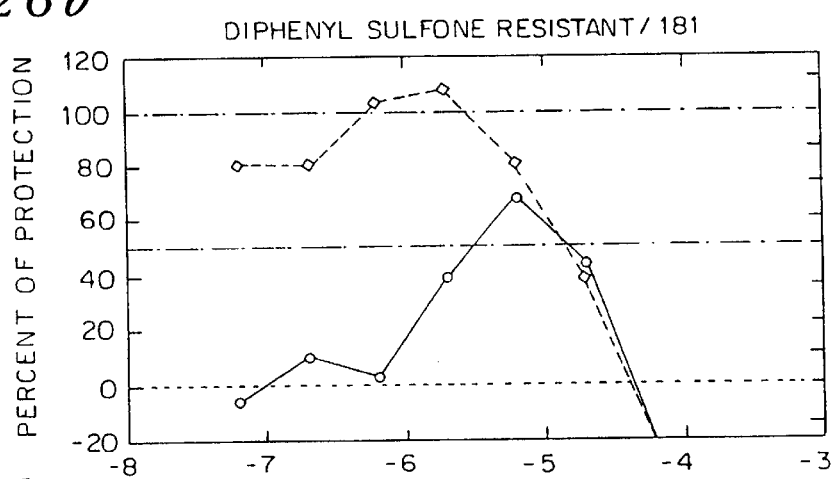
Figure 26C:
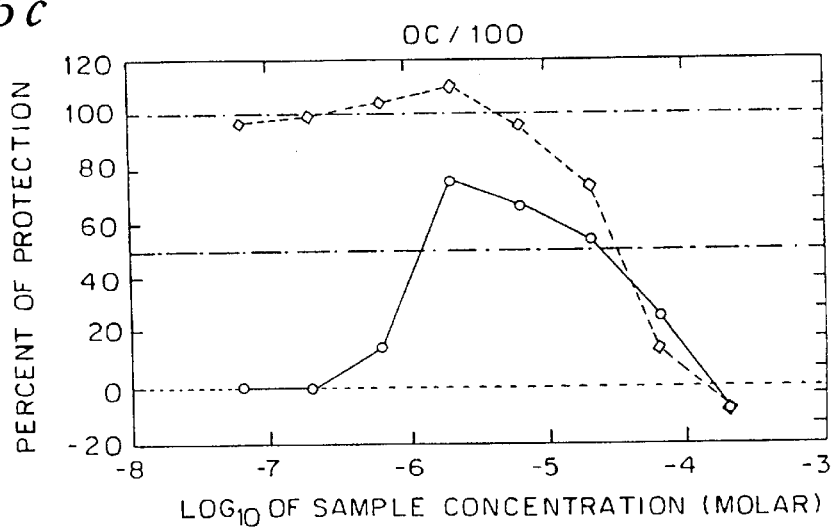
Figure 26D:
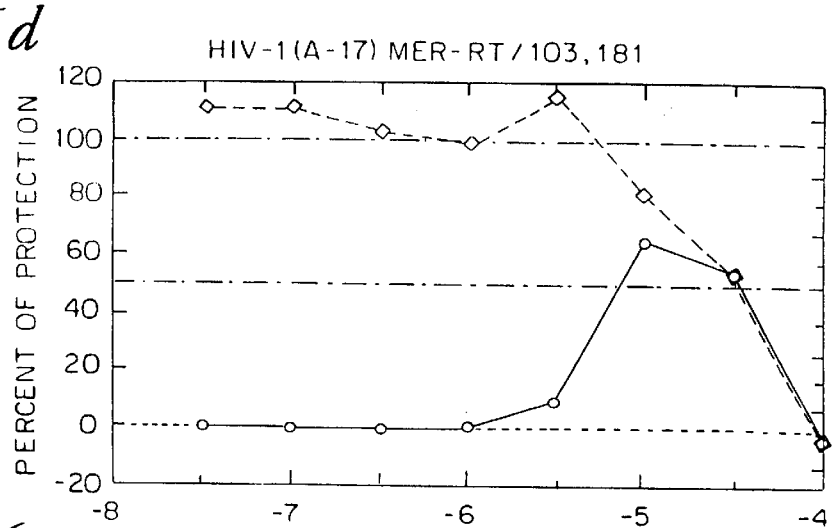
Figure 26E:
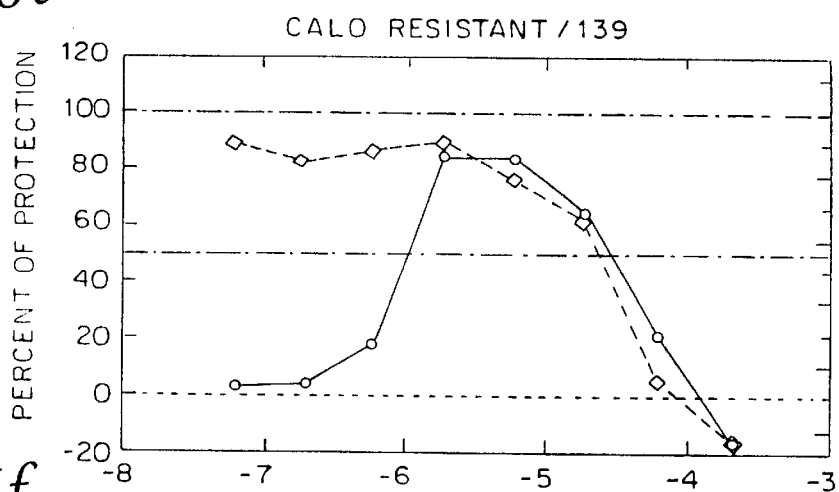
Figure 26F:
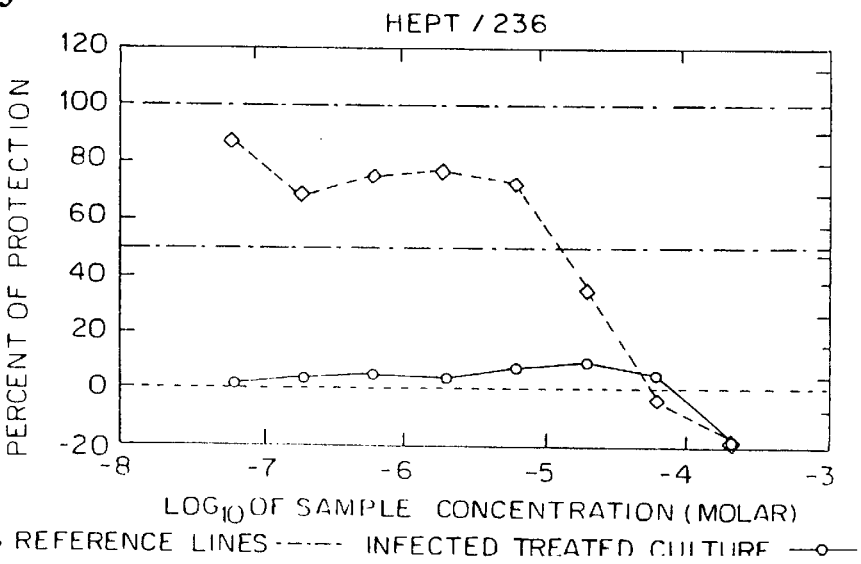
Figure 27:
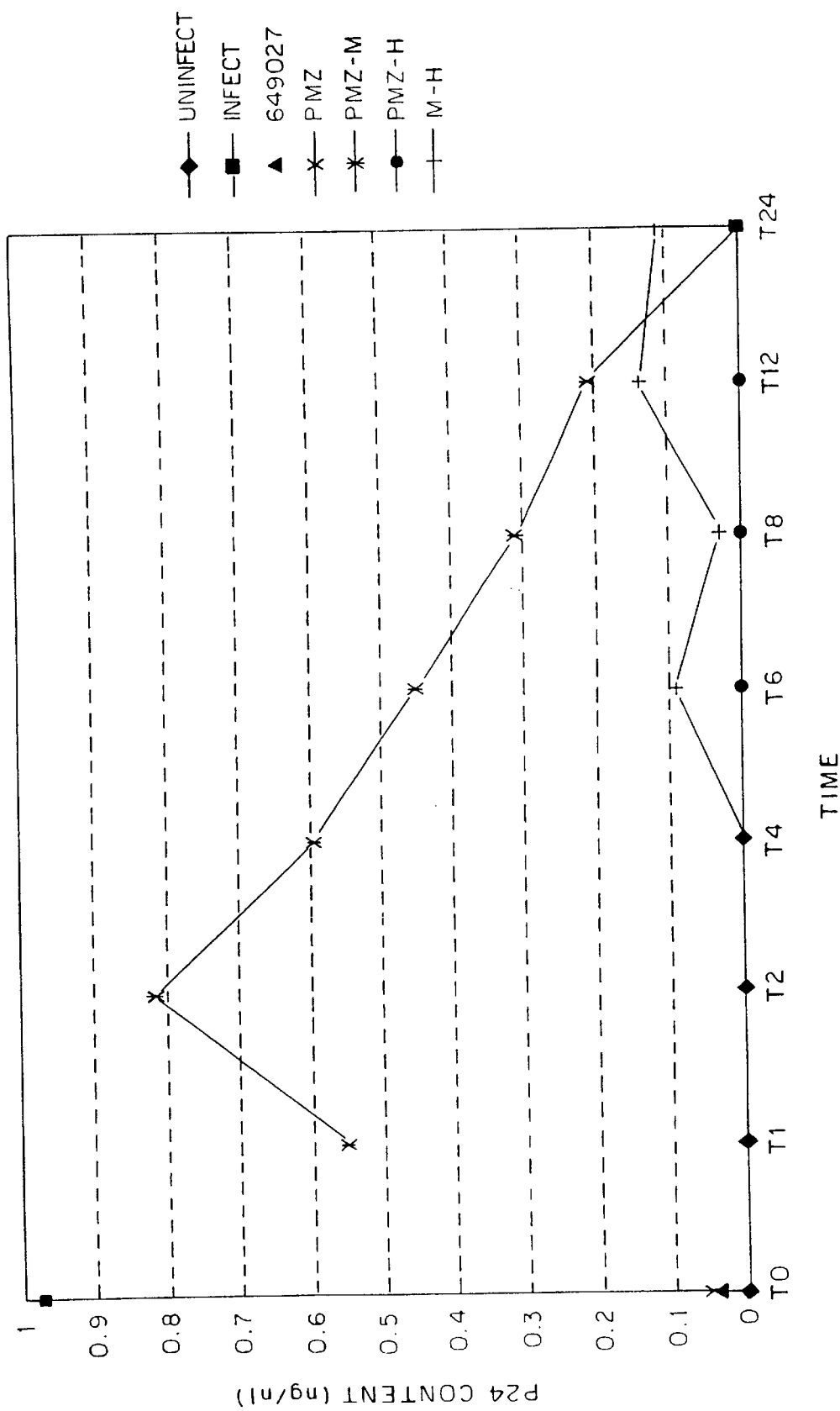
FIG. 27 is a graph showing time study of PMZ-1 versus HEPT.
Figure 28:
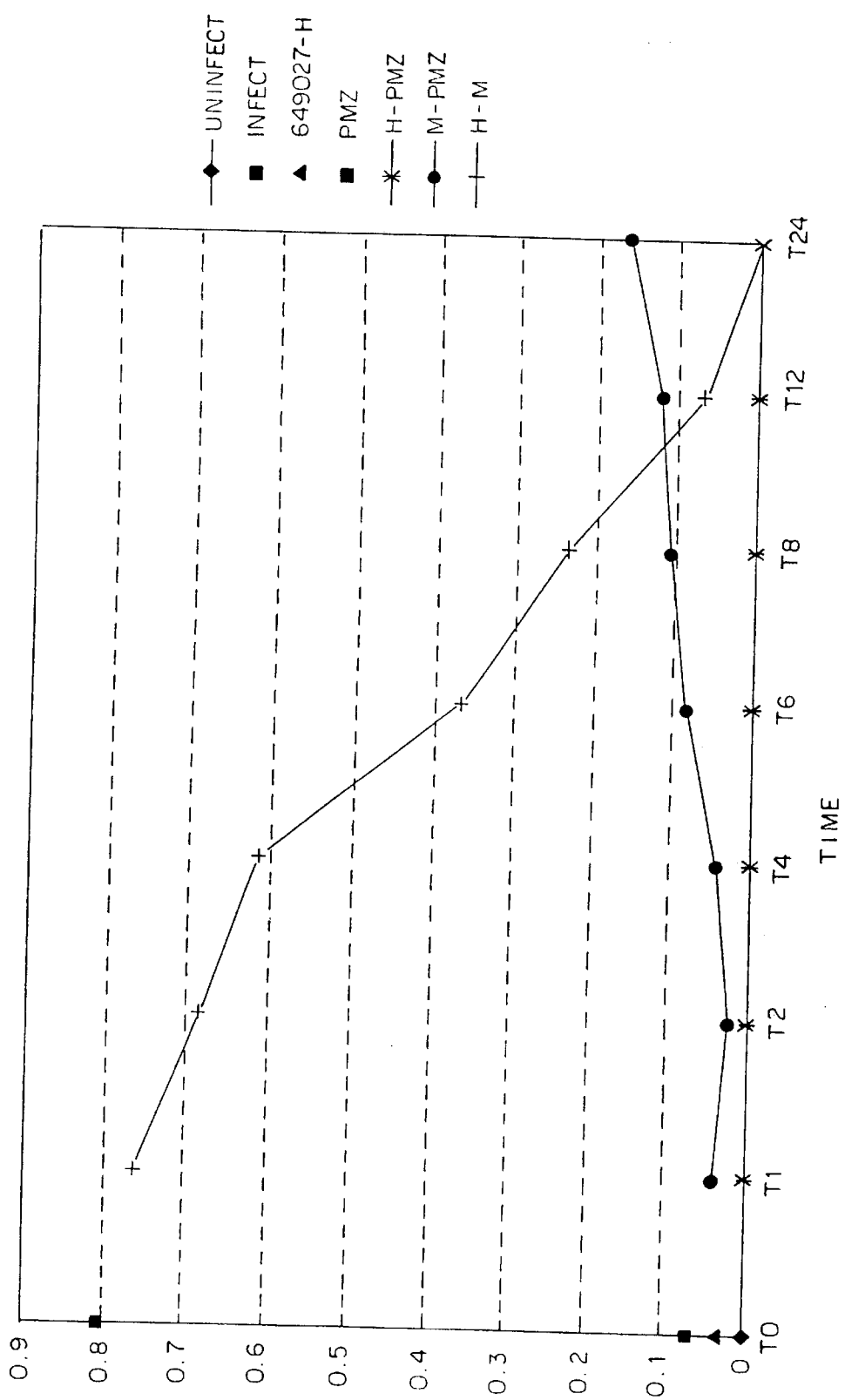
FIG. 28 is a graph showing time study of PMZ-1 versus HEPT.

PMZ-1 is active in the Mo/Mo assays as shown in FIG. 24, but has no effect on the attachment of virons on the cell receptors nor effect on the fusion of virons with the cells containing $CD_4$ receptors with those expressing viral envelop glycoproteins as shown in FIG. 23. The results for independent syncytia response for PMZ-1 on Magi cells are shown in FIG. 24.

The activities of PMZ-1 against various HIV mutants are shown in Table 6, and graphically presented in FIGS. 25 and 26.

TABLE 6

| Virus/Mutation | $EC_{50}$ (μM) | Fold Resistance |
| --- | --- | --- |
| HIV-1$_{1118}$ | 0.16 | sensitive |
| OC/L1001 | 0.43 | 2.7 fold |
| CALO/V901, P225S | 0.10 | sensitive |
| DPS/Y181C | 1.39 | 8.7 fold |
| A17/Y181C, K103N | 4.2 | 26 fold |
| HEPT/P236L | >5 | >31 fold |
| TiBO/A98G, V1081 | >5 | >31 fold |
| Thiazolo/V1081 | >5 | >31 fold |

Pharmacological studies of PMZ-1:

Pharmacological studies for PMZ-1 were carried out at NCI or through its contractors. The studies were designed to develop and to validate a suitable analytical method for the quantification of PMZ-1 in mouse, rat, and dog plasma with a concentration detection limit of 0.05 μg/ml. There was need to establish the stability of PMZ-1 in aqueous buffer solutions and in mouse, rat, and dog plasma at 37° C. and at 4° C. If decomposition of the drug is observed, the stability of PMZ-1 in frozen plasma and/or plasma extracts were to be determined for the purpose of studying sample handling and storage procedures. Studies were to be undertaken to determine the extent of protein binding of PMZ-1 in plasma of the mouse, rat, and dog in 0.1–10 μm range. Pharmacokinetics studies in $CD_2F_1$ mice were to be carried out to characterise the plasma concentration-time profiles after intravenous (i.v.) bolus administration at two dose levels. There was need to determine the oral bolus bioavailability studies of PMZ-1 as a route of administration.

Results and Discussion:

Solubility Studies:

PMZ-1 is soluble in ethanol (>1 mg/ml) and in 40% hydroxypropyl beta-cyclodextrin (HPCD) but poorly soluble in water. It is very soluble in propylene glycol (PG), polyethylene glycol (PEG) 400 and soybean oil. These solvents may be useful in formulating cosolvents suitable for pharmaceutical applications. The ethanolic solutions has UV absorptions in the 290–300 nm range, useful for analytical work. Aqueous solutions for analytical work were prepared in HPCD and diluted with water to the required concentrations. The stock solutions were stable when incubated for 48 hours at 37° C. and when stored at room temperature.

Stability Studies Results:

PMZ-1 is stable at room temperature for several months without detectable deterioration by TLC. Stock solutions in ethyl acetate have been used for TLC work over 8 months without decomposition. This observation suggests long shelf life for the compound.

Analysis of plasma samples taken from mice after the administration of PMZ-1 and stored at −20° C. for six weeks showed no obvoius changes of the ratio of the peak heights of the drug and the internal standard. Similar results were observed on the consistancy of the ratios of the peak heights of the putative metabolite and the parent drug for the stored samples. Table 7 summarizes the back-calculated concentration data for separate studies of the samples before aand after storage at −20° C. for six weeks. the numerical numbers are concentrations in units of μM.

TABLE 7

| | Before storage | After Storage |
| --- | --- | --- |
| Sample 1 | 25.6 | 23.3 |
| Sample 2 | 20.0 | 21.3 |
| Sample 3 | 9.2 | 10.2 |
| Sample 4 | 7.8 | 7.2 |

From the pharmacokinetics studies, PMZ-1 was unstable in 1.0 N hydrochloric acid (HCl) at 37° C., with 20% and 90% loss of parent compound after 3 and 24 hours of incubation, respectively. In 0.1 N HCl, only 10% degradation was observed after 24 hours. Loss of PMZ-1 was associated with the appearance of an earlier eluting peak. The compound was incubated in 1.0 N HCl at 60° C., all but 5% of PMZ-1 had degraded after 3 hours, and converted to a putative metabolite peak which eluded at 4 minutes. The rate of degradation of PMZ-1 was, however, slower when the experiment was repeated in 0.1 N HCl at 60° C. after 3 hours.

Figure 29A:
FIG. 29a is a graph showing HPLC traces of a water blank.
Figure 29B:
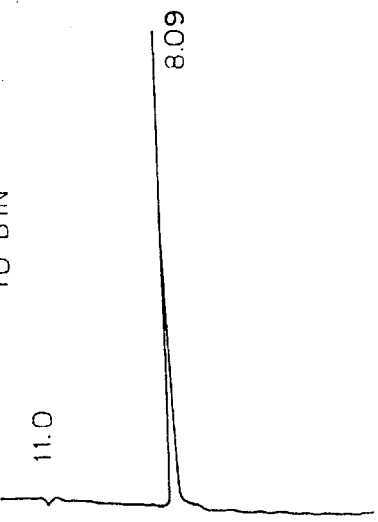
FIG. 29b is a graph showing HPLC traces for a 1 µM aqueous solution of PMZ-1.

Analytical Methods of Detection and Quantification:

Analytical methods for the analysis of biological fluids was carried out. The high pressure liquid chromatography (HPLC) method developed involved the use of Econosphere ODS stationary phase column. The elution was done with isocratically with (AcCN containing 0.02% triethylamine): water (1:1). Detection was by UV absorbance at 295 nm. FIG. 29 shows the HPLC traces of the water blank (a) and for 1 μM aqueous solution of PMZ-1 (b).

Figure 30A:
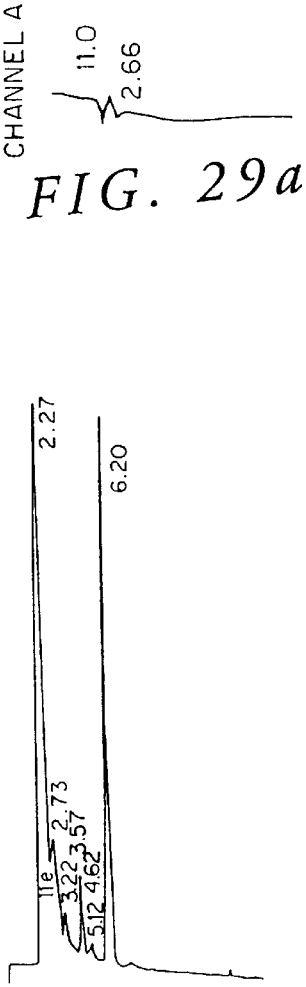
FIG. 30a is a graph showing traces of processed control mouse plasma.
Figure 30B:
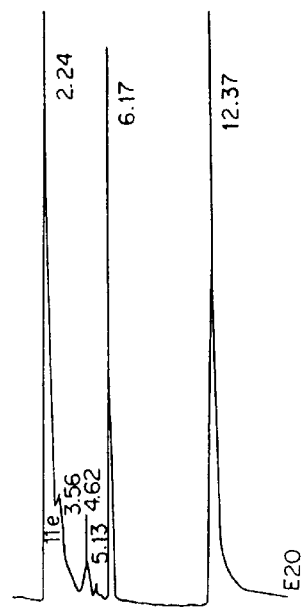
FIG. 30b is a graph showing a mouse plasma sample seeded with 50 µM of PMZ-1.

FIG. 30 shows the traces of processed control mouse plasma (a) and mouse plasma sample seeded with 50 μM of PMZ-1 (b). The peak at 6.26 minutes is that of an internal standard, acetophenone. PMZ-1 give a good correlation coefficients (>0.99) between concentration and peak heights in the concentration ranges 1–100 $\mu$M both in aqueous and processed mouse plasma.

Figure 31A:
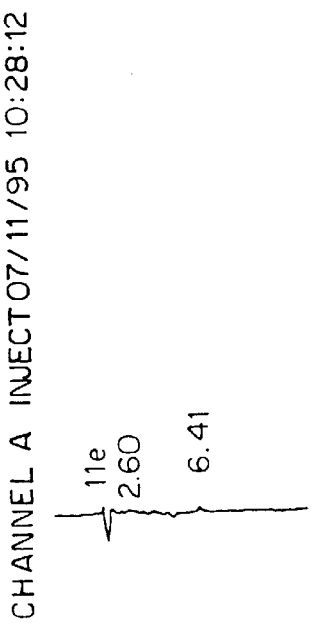
FIG. 31a is a graph showing preliminary pharmacokinetics studies of PMZ-1 in mice after intravenous administration of 20 mg/kg using HPCD as a vehicle, wherein water is the blank.
Figure 31B:
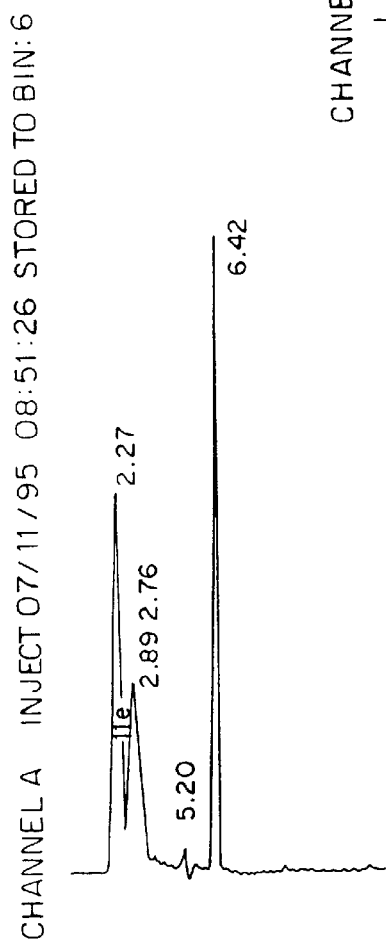
FIG. 31b is a preliminary pharmacokinetics study of PMZ-1 in mice after intravenous administration at 20 mg/kg using HPCD as a vehicle, in which there is control processed plasma.

Bioavailability:

Preliminary pharmacokinetics studies of PMZ-1 in mice after intravenous administration at 20 mg/kg using HPCD as a vehicle were carried out. The results are shown in FIG. 31, which shows water blank (a), control processed plasma (b) and processed plasma from a mouse after 15 minutes of intravenous dosing with 20 mg/kg. The peak at 6.4 minutes is that of the internal standard while that at 12.9 minute corresponds to PMZ-1.

Figure 31C:
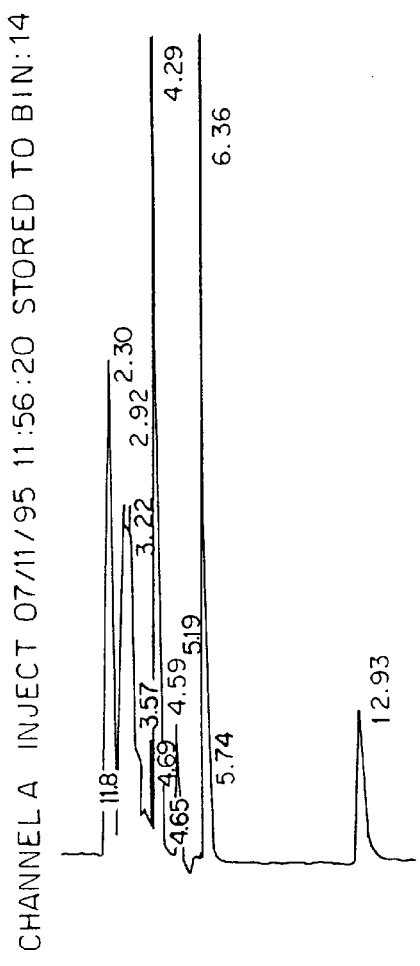
FIG. 31c is a graph showing preliminary pharmacokinetics studies of PMZ-1 in mice after intravenous administration of 20 mg/kg using HPCD as a vehicle, in which processed plasma from a mouse after 15 minutes of intravenous dosing with 20 mg/kg, wherein the peak after 4.29 minutes refers to a putative metabolite of PMZ-1.

The peak after 4.29 minutes in FIG. 31c refers to a putative metabolite of PMZ-1. Its height is propotional to the decrease of the peak height of PMZ-1 at 12.39 minute after drug intravenous administration.

Mouse plasma samples were prepared for HPLC analysis by treatment with MeOH containing 0.3% perchloric acid. This system gave very good reproducible results Drug recovery was ≈85%. The current limit of detection (LOD) at the wavelength of 295 nm for PMZ-1 in mouse plasma is 0.1 $\mu$M.

The drug appears to be eliminated rapidly from the plasma. When PMZ-1 was administered i.v. to mice in hydroxypropyl-beta-cyclodextrin (HPCD) at 50 mg/kg, peak plasma levels of 20–25 $\mu$M (2–15 minutes) fell rapidly to 0.3 $\mu$M 180 minutes. Administration of 100 mg/kg in HPCD was associated with neurotoxicity (seisures 1–30 minutes after dosing, followed by lethargy). However, the mice appear normal 2 hours after drug administration. When PMZ-1 was administered in 50% polythene glycol (PEG) 400 in water (50:50), similar toxicity was observed at 50 mg/kg. Studies using PEG 400 and water (50:50) for intravenous administration of PMZ-1 at lower dose of 20 mg/kg, central nervous system (CNS) toxicity was observed as disorientation but no seisures were observed. The drug elimination was much faster than when HPCD was used as the vehicle of administration. The drug plasma concentration reached 41 $\mu$M, 5 minutes after intravenous administration. The sharp increase in absorption after 4 minutes corresponse to the putative metabolite while the peak at 5.82 minutes is that of the internal standard, acetophenone. Studies indicate some bioavailbility of PMZ-1 after i.p. and s.c. administration at 50–100 mg/kg. Plasma levels declined rapidly after dosing, reaching the limit of assay sensitivity by 120–180 minutes. Oral bioavailbility is very low with substantial compound found in the GI tract after a 250 mg/kg dose.

Figure 32B:
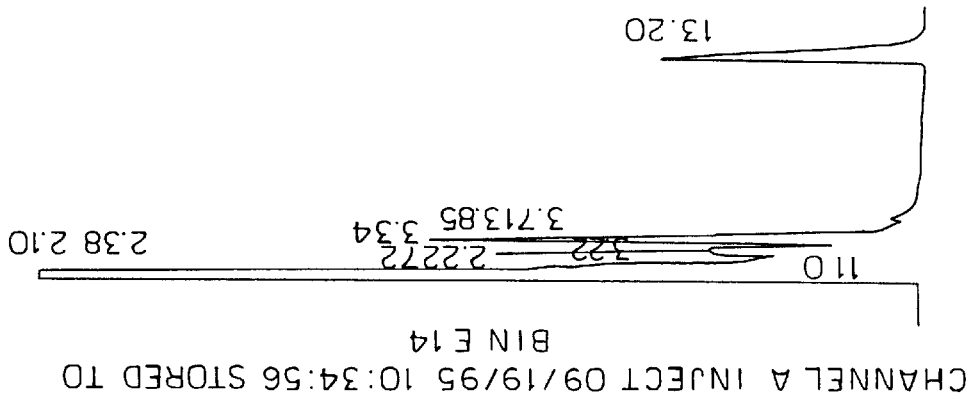
FIG. 32b is a graph showing the HPLC traces for the solution in mouse plasma of 10 μM of PMZ-1.
Figure 32A:
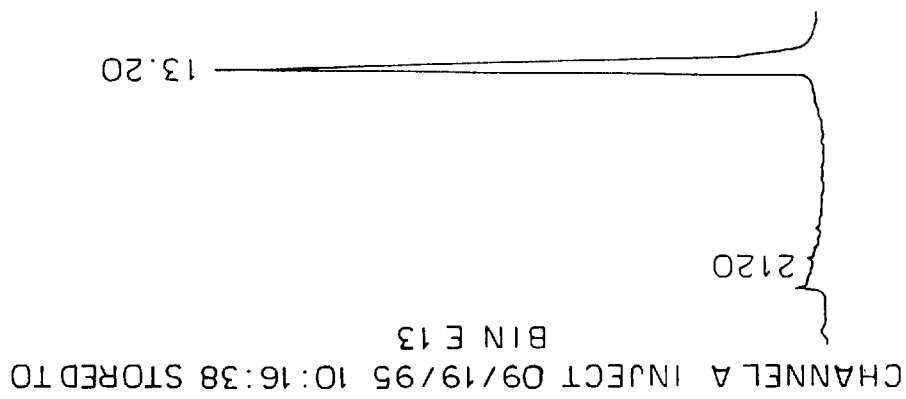
FIG. 32a is a graph showing the HPLC traces for the ultrafiltrates (30 kD nominal cutoff) of an aqueous solution.
Figure 33A:
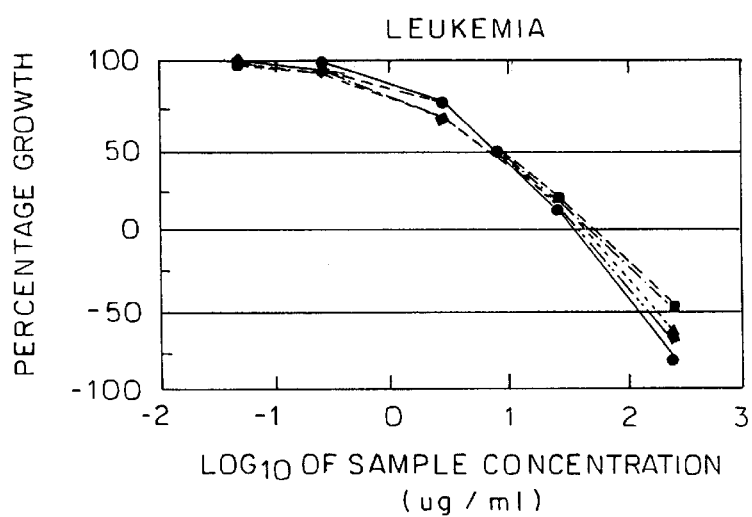
Figure 33B:
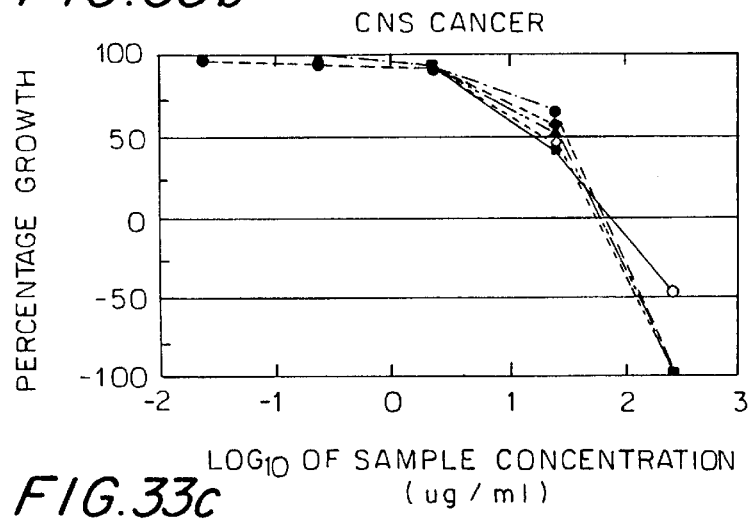
Figure 33C:
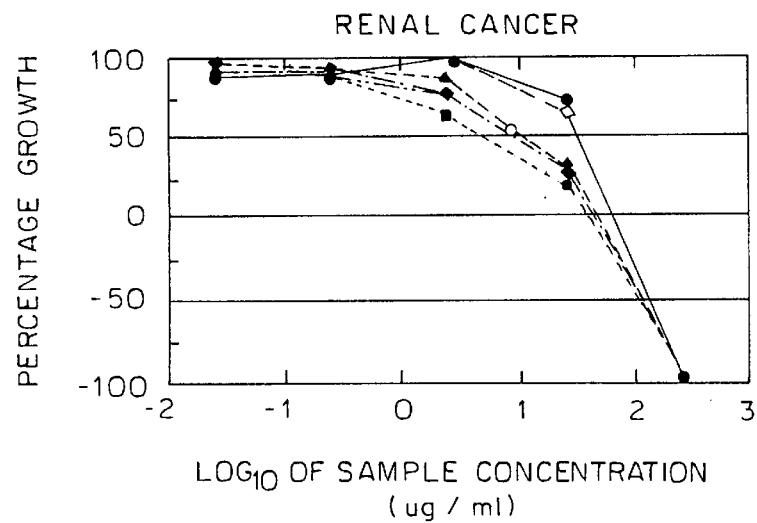
Figure 33G:
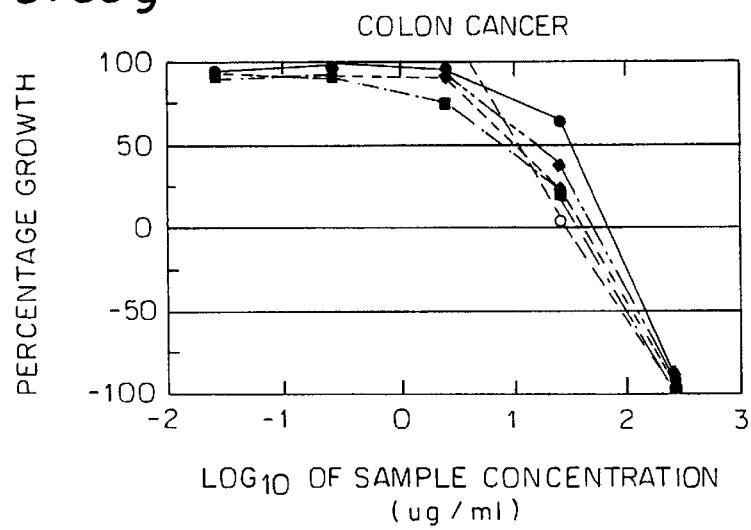
Figure 33H:
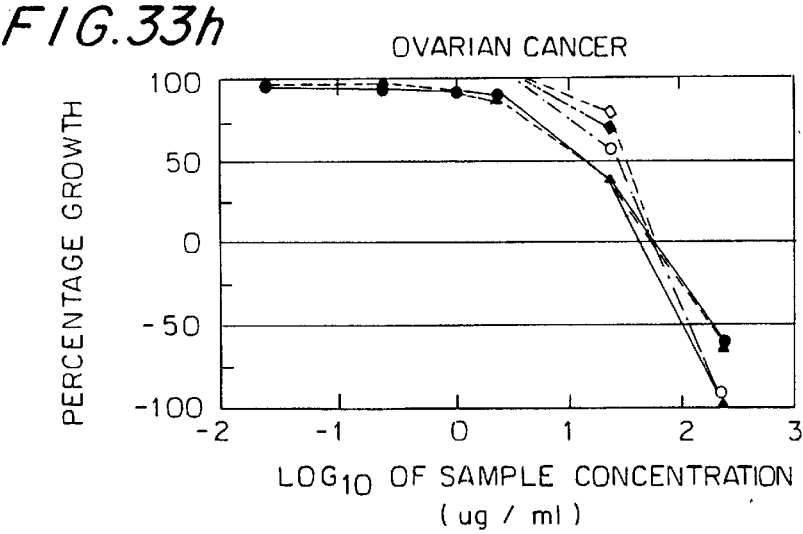
Figure 33I:
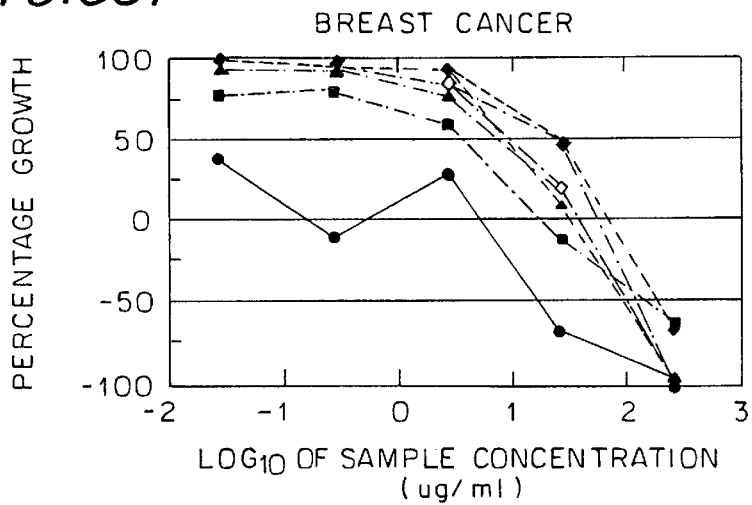

Protein Binding:

From the protein binding studies of PMZ-1 to constituents of mouse plasma, it was observed that the recovery of the drug was 45–50% in the were carried out by interaction of PMZ-1 with model protein BSA, using fluorescence spectroscopy as the analytical tool. The studies demonstrated concentration dependent quenching of fluorescence of BSA by concentration of PMZ-1 in the $\mu$M range. FIG. 32 shows the HPLC traces for the ultrafiltrates (30 kD norminal cutoff) of an aqueous solution (a) and for a solution in mouse plasma (b) of 10 $\mu$M of PMZ-1. PMZ-1 is present in the urine after parenteral and non-parenteral administration. The drug was also detected readily in liver, kidneys and small intestine tissue samples taken during the first 60 minutes after intraveneous administration at 10 mg/kg body weight of a mouse. An earlier eluting peak representing a possible metabolite was also observed in the urine. The presence of this peak in plasma after oral administration is suggestive of first-pass metabolism.

Hollow Fibre Studies:

Preliminary studies show that PMZ-1 is active when tested intraperitoneally.

Summary Discussion

The compound, PMZ-1, is a natural product extracted from stem bark, leaves and root bark of a Zimbabwean medicinal plant, *Bolusanthus speciosus*. The plant is locally known as mupaka (Shona) and impaca (Ndebele). *B. speciosus* is a deciduous tree common in all parts of Zimbabwe, (*A Rhodesian Botanical Dictionary of African and English Plant Names*, H. Wild revised by H. M. Biegel and S. Mavi, National Herbarium, Department of Research and Specialist Services, Ministry of Agriculture; Printed by Government Printer, Harare, Zimbabwe). Its distribution is wide spread throughout the country at low to medium attitudes. It grows to the height of about 4 meters attaining its largest size on termite mounts. It is found in woodlands usually on sand clay and on rocky grounds. The wood is very durable and resistant to termite attack.

Traditionally, the plant is used as a herbal remedy as bile emisis (leaves), for abdominal pains (root bark) and is used to induce vomiting (root bark).

PMZ-1 was isolated from *Bolusanthus speciosus* (Bolus) Harms collected from the National Herbarium Botanical Garden, Harare, Zimbabwe on Jun. 16, 1993. The voucher specimen can be viewed at this venue, Main Herbarium Accession #285825 and Collector's #106. Followup samples were collected from other part of Zimbabwe.

PMZ-1 is active against HIV-$1_{RF}$ (EC$_{50}$=0.1 $\mu$M) and HIV-$1_{IIIB}$ (EC$_{50}$=0.2 $\mu$M) in the United States of America National Cancer Institute's AIDS anti-viral screen, with cytotoxic concentrations (IC$_{50}$) of 30 to 50 $\mu$M respectively. This suggests that PMZ-1 has a broad therapeutic index (TI>300). PMZ-1 shows good activity when tested in the fresh human peripheral blood mononuclear cells (PBMC's, EC$_{50}$<1 $\mu$M) and monocytes/macrophages (Mono/Mac's, EC$_{50}$<1 $\mu$M) assays. But PMZ-1 shows weak activity against both HIV-2 and simian immunodeficiency virus (SIV) viruses. PMZ-1 exhibit a pattern of activity against mutant HIV viral strains indicating its non-nucleoside reverse transcriptase inhibitory (NNRTI) activity. PMZ-1 is active against azidothymidine sensitive and resistant (AZT$^{sen}$ and AZT$^{res}$) as well as 2',3'-dideoxy-inosine (ddI) mutants. However, the compound shows a weak activity against viruses containing mutations in reverse transcriptase (RT) codons affecting nonnucleoside reverse transcriptase inhibitors (NNRTIs). The compound, shows reasonable activity (EC$_{50}$≈1.0 $\mu$M) against mutants, Y181 and L100I, which frequently arise during NNRTI clinical treatments and affecting general of structural types of NNRTIs. PMZ-1 has demonstrated moderate activities against mutants, isolated by Merck Sharp & Dohme Research Laboratories, which exhibits two mutations in the reverse transcriptase domain at codons 103 and 181. The compound also exhibits some activity against three other mutant viruses containing reverse transcriptase domain at codons 181, 139 and 100. Although the pattern against mutant viral strains suggests that PMZ-1 is a NNRTI, the compound exhibits some activities against HIV-2 and SIV a property not usually associated with NNRTIs. The fact that PMZ-1 shows activity against double mutant strain and mutant strains 181, 139, and 100 warrants further studies. Virtually all NNRTIs studied so far are totally inactive against mutant virus 100. It is necessary to carry out assessment studies of PMZ-1 as a complementary drug with other NNRTI's. Preliminary combination studies indicate that PMZ-1 exhibits anti-viral synergistic effects when administered in combination with AZT. The testing of PMZ-1 in combination with other agents is ongoing.

The mechanism-of-action studies have shown that while PMZ-1 shows enzymatic activity of HIV-1 reverse transcriptase ($ID_{50}$=0.043 $\mu$M) using the template/primer, rC/dG, the compound is less active when the rA/dT template/primer is used ($ID_{50}$=3.0 $\mu$M). This level of activity is also observed with other NNRTIs. It inhibited protease enzymatic activity ($ID_{50}$=3.8 $\mu$M) and integrase enzymatic activity ($ID_{50}$=40 $\mu$M). The polymerase chain reaction (PCR) time course studies confirm the anti-reverse transcriptase activity in infected cells. Other time course studies in which PMZ-1 is added at various times after infectious cycle suggest that there are possibilities of other activities of PMZ-1, in addition of its inhibition of reverse transcriptase viral enzyme.

PMZ-1 shows no effect on the attachment of virons to cells no on fusion of cells containing $CD_4$ receptor with those expressing viral envelope glycoprotein. The interaction of $gp120^{env}$ protein of the HIV-1 virus and $CD_4$ at the cell surface is necessary for the viral entry into the host cell. The interaction of $gp120^{env}$ of infected infected $CD_4$ with non-infected $CD_4$ causes cell aggregation leading to the proliferation of the virus.

A polymerase chain reaction (PCR) time-course study has confirmed the activity of PMZ-1 against HIV-1 RT in infected cells. In other time-course studies in which PMZ-1 was added at various times after infection up to 28 hours postinfection) suggest that PMZ-1 exhibits other biological activities in addition to inhibition of RT. When PMZ-1 is compared with nevirapine, a typical NNRTI, nevirapine is only effective when added to culture within the first 8 hours (before the period in which DNA synthesis occurs) after infection of the cells. In contrast, PMZ-1 is effective even after DNA synthesis has occurred. The XTT cytoprotection and inhibition of p24 production are observed when PMZ-1 is added after reverse transcriptase has been completed.

Based on the data presented, PMZ-1 is NNRTI with a novel chemical structure and unique properties that acts intracellularly against the reverse transcriptase (RT) viral enzyme and possibly against other viral enzymatic targets. The possibility of PMZ-1 attacking multiple targets will have important clinical application. More definitive studies to understand the mechanism(s) of action of PMZ-1 against HIV-1 virus are in progress. Better elucidation of the pattern of activity of PMZ-1 against HIV-1 variants with site directed mutations affecting NNRTI's is also in progress. Detailed studies using drug resistant strains are important in order to evaluate the total effect of inhibition against HIV mutants. There is need for better assessment of the role of anti-protease and anti-integrase activities of the HIV-1 production. Preliminary formulation, pharmacokinetics, quantitative assays, bioavailability, and toxicological studies are necessary to assess the clinical potential of PMZ-1 as an anti-HIV-1 chemotherapeutic drug.

Oral administration of 3×1 mg of PMZ-1 per day for three days to this inventor resulted in total cure of his 20 year old athlelet's foot fungal infection. PMZ-1 will be evaluated for its possible anti-fungal and antimicrobial activities.

PMZ-1 is easily extracted from the natural sources but its simple structure suggests that the compound can be synthesized in the laboratory by such persons as skilled in the art. Additionally, structural activity relationships (SAR) studies of PMZ-1 are in progress with the aim of improving both the integrase and protease activities. Table 8 below gives the summary of activities of PMZ-1.

TABLE 8

| Parameter | Findings |
| --- | --- |
| gp 120-$CD_4$ Binding | No Binding |
| HIV-1 Attachment to CEM-SS cells | No inhibition at 100 $\mu$M |
| Inhibition of RT Activity in virons | $ID_{50}$ = 1.2 and 4.8 $\mu$M using rA/dT |
| | $ID_{50}$ = 43 and 72 nM using rC/dG |
| Integrase activity | $ID_{50}$ = 40 $\mu$M |
| Inhibition of purified protease | $ID_{50}$ = 3.8 $\mu$M |
| U1/TNF$\partial$ Latent Infection | XTT: Toxic at $\leq$3.16 $\mu$M but fine at 1 $\mu$M |
| | p24: no inhibition of p24 production |
| Time Course Assay (1 $\mu$M) | PCR: Profile of RT inhibition PCR signal at Pre only and at 4 hours. No PCR product at Pre/$t_0$, $t_0$, $t_{0.5}$, $t_1$ or $t_2$ |

PMZ-1 Activity in Cancer Assays:
PMZ-1 Activity in Cancer Assays:

PMZ-1 shows good activity against breast cancer when tested in the 60 cell line panel. PMZ-1 is active and selective for the MCF7 cell line at lower concentration <0.025 $\mu$g/ml. The results of these studies are shown in Table 9 and FIGS. 33, 34 and 35.

Cancer Data Interpretation:

The cancer data for PMZ-1 in this application were recorded at the National Cancer Institute, USA. Table 9 is the record of the experimental optical densities as a factor of logarithmic concentrations of the sample tested. The table shows 9 major cancer cell lines along with the sub-cell lines for each major cell line. The percent growth (PG) refers to the percentage increase of the mass/numbers of cells being tested as compared to the cells in the control. The response factors $GI_{50}$, TGI and $LC_{50}$ are calculated based on the values of PG and are defined: $GI_{50}$(PG=+50) the concentration of PMZ-1 required to cause test cells to grow only 50% as compared to the growth of the cell in the control. TGI (PG=0) the concentration of PMZ-1 for which the masses of the cells in the control and in the test wells are equal. At this concentration, the cell growth is supressed. $LC_{50}$ (PG=50) the concentration for which the masses of the cell in the test well are only 50% of those in the control.

Figure 34:
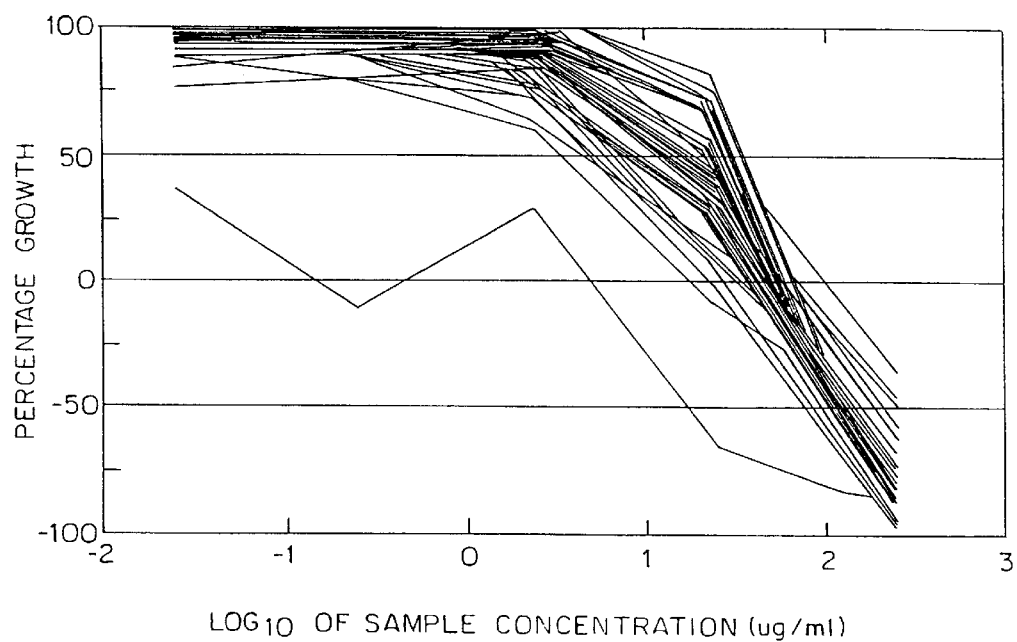
FIG. 34 is a graph showing results of all cell line responses combined.
Figure 35A:
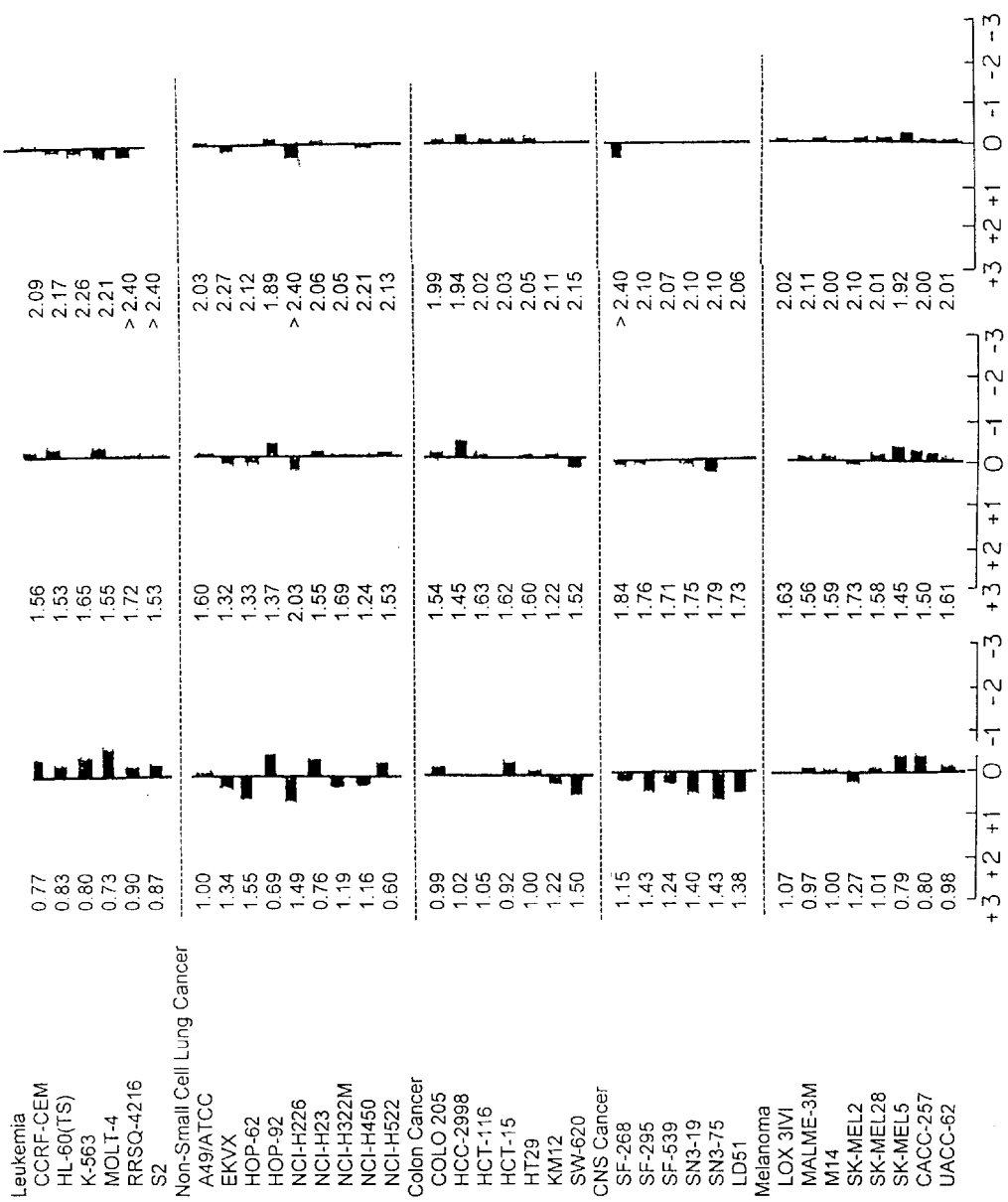
FIG. 35 is a chart showing the mean graphs from the response parameters $GI_{50}$, TGI and $LC_{50}$.
Figure 35B:
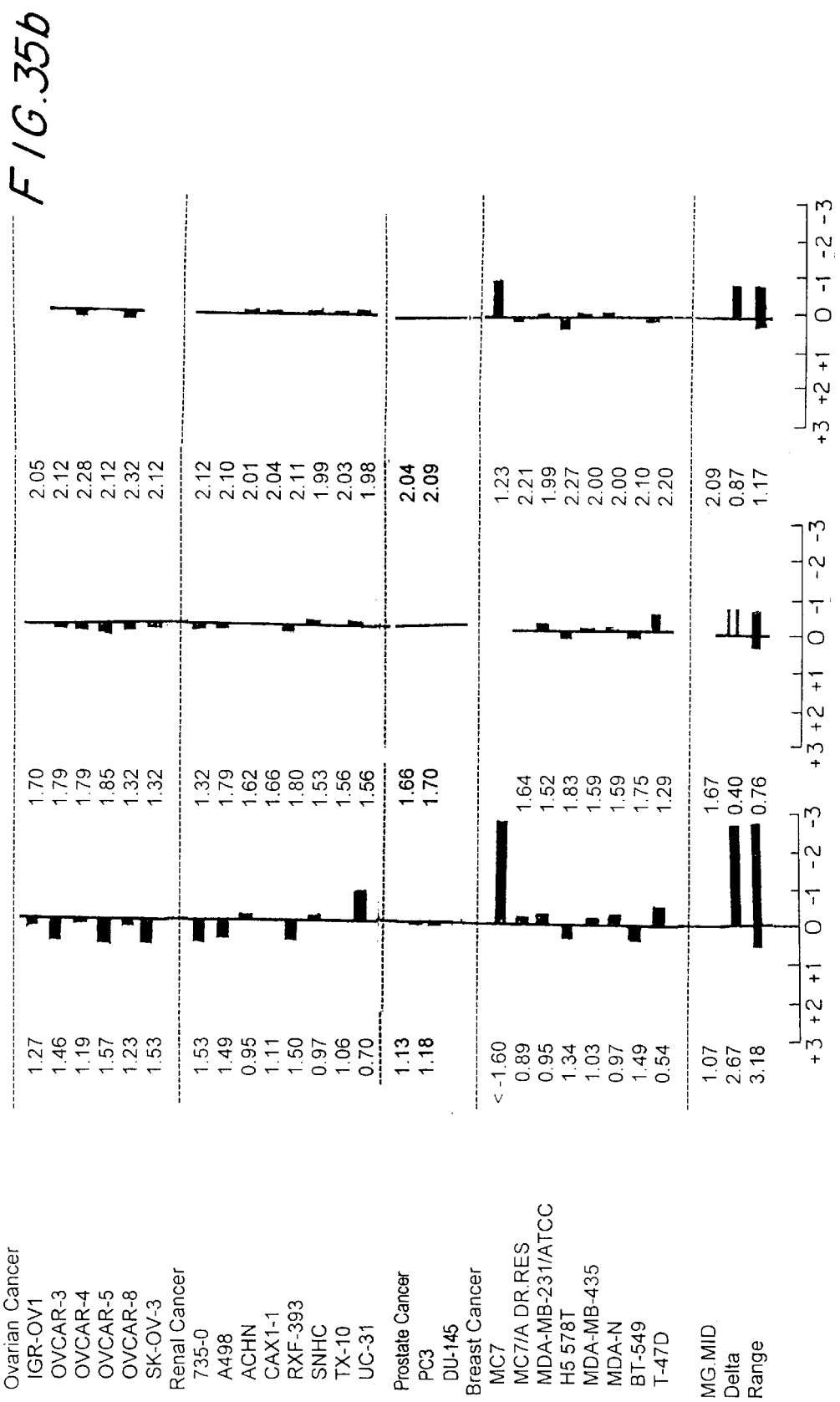

FIG. 33 shows the dose-response curves for PMZ-1 derived by plotting PG vs $log_{10}$ values of the appropriate concentrations for each cell line. The curves are grouped by subpanels of the major group. $GI_{50}$, TGI and $LC_{50}$ from the point each curve crosses PG line +50, 0 and −50 respectively. FIG. 34 shows all cell line responses combined. FIG. 35 shows the mean graphs from the response parameters $GI_{50}$, TGI and $LC_{50}$. The centre line represent athe average response of all cell lines to the drug. For each group and subpanels, bars extending to the right are more sensitive to the drug than the average, and those extending to the left are less sensitive.

The compound PMZ-1 shows the greatest sensitivity against brest cancer subpanel MCF7 with $GI_{50}$ and $LC_{50}$ at <0.025 $\mu$g/ml and 16.8 $\mu$g/ml respectively. PMZ-1, along with its analogs, has a potential to be developed into useful chemotherapeutic compounds against breast and other cancers.

Future Prospects for PMZ-1 Analogs:

Based on this full disclosure of this invention, it will be obvious to those skilled in the art that many changes and modifications can be made without departing from the scope and the spirit of this invention. It is understood that in vitro data can be used to determine effective human dose.

Figure 12:
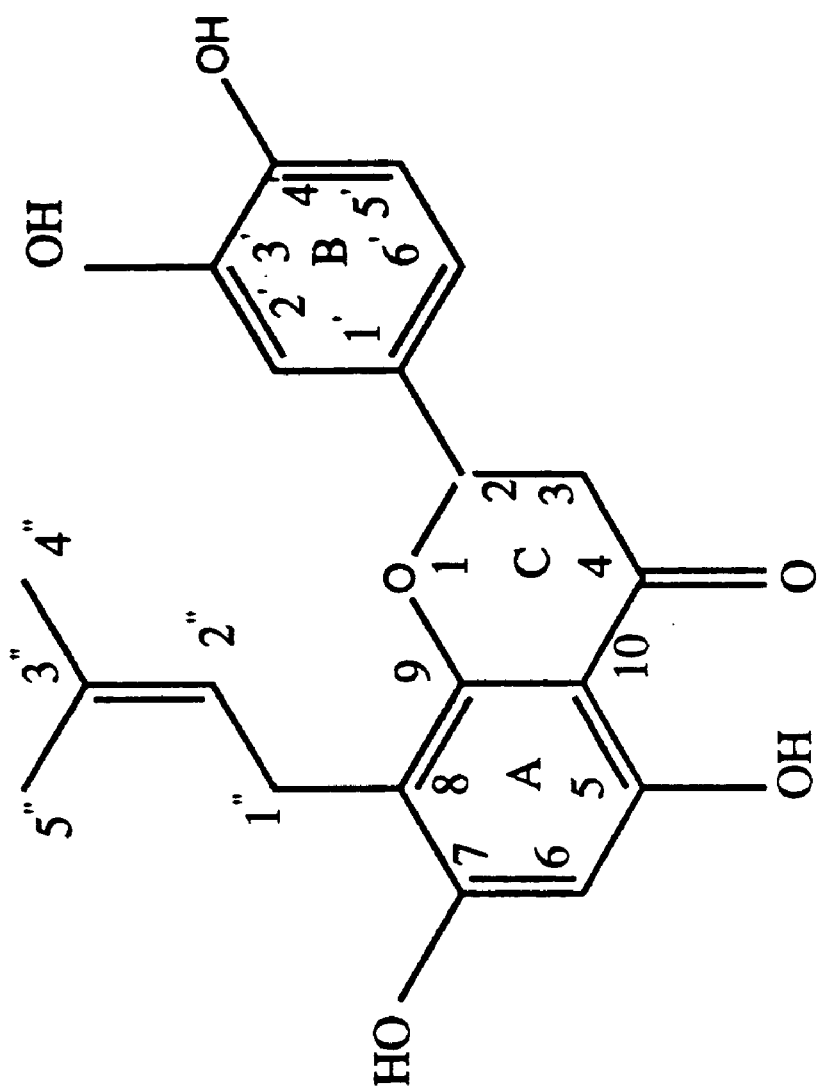
FIG. 12 shows the structural formula of a compound which is devoid of HIV activity and which was also isolated along with PMZ-1.
Figure 13:
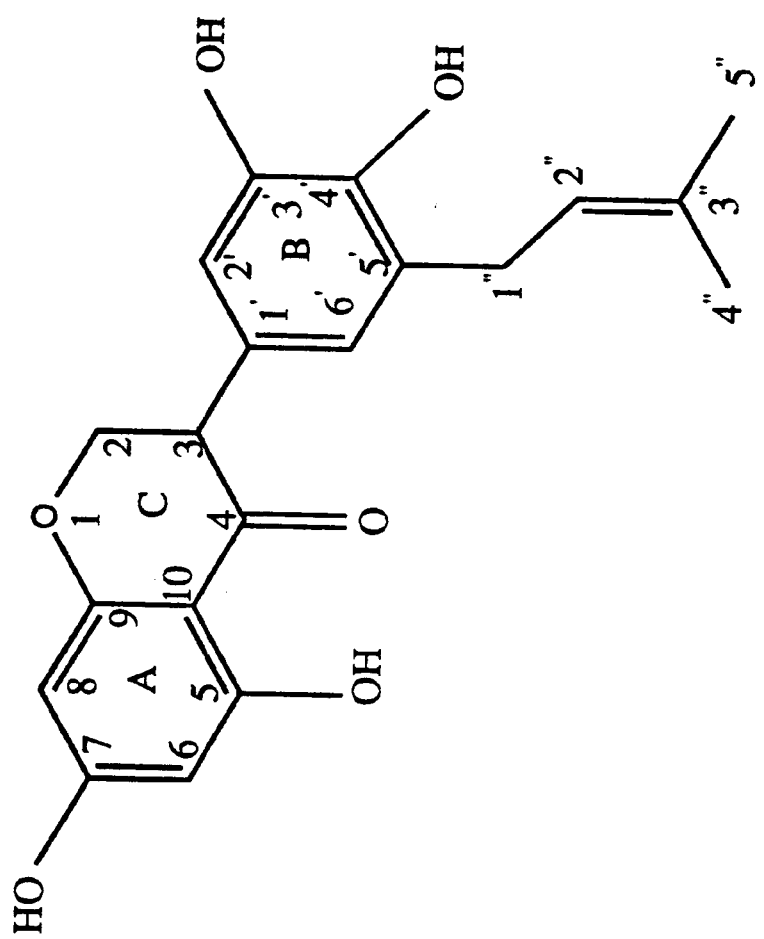
FIG. 13 shows the structure of a compound, which was also isolated along with PMZ-1 and that is devoid of HIV activity.

In order to completely evaluate the potential of PMZ-1 as a clinical chemotherapeutic agent as anti-HIV and cancer, a number of closely related compounds to PMZ-1 can be synthesized in the laboratory. These analogs can be prepared and evaluated with the main aim of improving anti-HIV activities in the integrase and protease assays. Structural relationship analysis of PMZ-1 and those shown in FIGS. 12 and 13 indicates that the origin of activity of PMZ-1 and lack of activity of the structures oin FIGS. 12 and 13 is due to inability of the pentenyl group at 5' to cyclize as the ortho OH group is methylated. The availability of the pentenyl is necessary for the anti-HIV activity of this class of compounds.

Compounds of the general formula in formula 1 can be synthesized in a laboratory without departing from the scope of this invention. The modification on the flavanone or iso-flavanone can be designed to make the analogs more bioavailable in a mammal. Flavanoids, isoflavanoids and dihydro-derivatives lacking prenylation substitution would be expected to be inactive against HIV virus.

Formula I

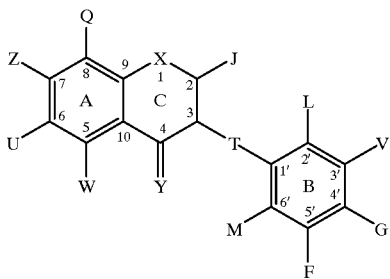

in which the 2-3 bond in ring C could be a double or single bond. Ring B and its substituents may be attached at position 2 (at J) in ring C. The key feature in the modifications is that the prenylation must not cyclize through the free OH group (s) at ortho position to the prenylation. Atoms attached at X in ring C may be S or N or P or C or O or pharmaceutically acceptale metal or $CH_2$. Atoms attached to Y could be S or N or P or O or alkyl ($C_1$–$C_8$) or alkoxy ($C_1$–$C_8$) or alkylthio ($C_1$–$C_8$) or aryloxy ($C_6$–$C_{10}$) or alkoxycarbonyl ($C_2$–$C_8$) or heterocycloalkoxy ($C_2$–$C_{10}$) pharmaceutically acceptable metal or $CH_2$ or the like; the prenylation could be attached at any position L or V or G or F or M or W or U or Z or Q; the prenylation could be singly or multiple or in combination; the prenylation could be penteny group (—$CH_2$—CH=C($CH_3$)$_2$) or geranyl (—$CH_2$CH=C(Me)$CH_2CH_2$CH=C(Me)$_2$) or lavandulyl (—$CH_2$—CH(C($CH_3$)=$CH_2$)$CH_2CH$=C($CH_3$)$_2$) or -o-pentenyl (—O—$CH_2$—CH=C($CH_3$)$_2$) or -o-geranyl (—o-$CH_2$CH=C(Me)$CH_2CH_2$CH=C(Me)$_2$) or -o-lavandulyl (-o-$CH_2$—CH(C($CH_3$)=$CH_2$)$CH_2CH$=C($CH_3$)$_2$) or substituted pentenyl, geranyl and lavandulyl with hydroxy, alkoxy ($C_1$–$C_8$), alkylthio ($C_1$–$C_8$), aryloxy ($C_6$–$C_{10}$), alkoxycarbonyl ($C_2$–$C_8$) or heterocycloalkoxy ($C_2$–$C_{10}$) or halogen; on the ortho positions of the above groups could be substituted with veratryl or anisyl or epoxyangelyl or isobutanolyl or angelyl or 6-dimethylpyrane or formylloxy or isoamyl or 3-methylbutyl or -o-heterocycle ($C_2$–$C_{10}$) or alkoxy ($C_1$–$C_8$) or alkylthio ($C_1$–$C_8$) or aryloxy ($C_6$–$C_{10}$) or alkoxycarbonyl ($C_2$–$C_8$) or heterocycloalkoxy ($C_2$–$C_{10}$) or amino ($NH_2$) or glycosides (1–10 sugar units) or o-glycosides (1–10 units) or oxyacetic acids or Schiff base or dialkylaminoalkyl ($C_1$–$C_{10}$) or amino acid esters ($C_1$–$C_{10}$) or extended amines ($C_1$–$C_{10}$, $N_1$–$N_6$) or sulphate esters or flavan or substituted aryl groups with alkyl ($C_1$–$C_{10}$) or phenoxy or alkenyl ($C_3$–$C_8$) or phenyl substituted with one to three groups, these being hydroxy, halogen, or alkynyl ($C_2$–$C_8$) or nitro or cyano or acetates, any position L or V or G or F or M or W or U or Z or Q which are not substituted with the prenylation as above may be substituted such as to prevent internal cyclization of the of the prenylation, groups which can be attached to L or V or G or F or M or W or U or Z or Q could be alkoxy ($C_1$–$C_8$), alkylthio ($C_1$–$C_8$), aryloxy ($C_6$–$C_{10}$), alkoxycarbonyl ($C_2$–$C_8$) or heterocycloalkoxy ($C_2$–$C_{10}$) or halogen or veratryl or anisyl or epoxyangelyl or isobutanolyl or angelyl or 6-dimethylpyrane or formylloxy or isoamyl or 3-methylbutyl or -o-heterocycle ($C_2$–$C_{10}$) or alkoxy ($C_1$–$C_8$) or alkylthio ($C_1$–$C_8$) or aryloxy ($c_6$–$C_{10}$) or alkoxycarbonyl ($C_2$–$C_8$) or heterocycloalkoxy ($C_2$–$C_{10}$) or amino ($NH_2$) or glycosides (1–10 sugar units) or o-glycosides (1–10 units) or oxyacetic acids or Schiff base or dialkylaminoalkyl ($C_1$–$C_{10}$) or amino acid esters ($C_1$–$C_{10}$) or extended amines ($C_1$–$C_{10}$, $N_1$–$N_6$) or sulphate esters or flavan or substituted flavan or substituted aryl groups with alkyl ($C_1$–$C_{10}$) or phenoxy or alkenyl ($C_3$–$C_8$) or phenyl substituted with one to three groups; these being hydroxy (except ortho to prenylation), halogen, or alkynyl ($C_2$–$C_8$) or nitro or cyano or acetates or saturated or unsaturated aliphatic ($C_2$–$C_8$), cycloaliphatic ($C_1$–$C_{15}$) or aromatic hydrocarbonyl ($C_1$–$C_{15}$) or bridged cycloaklyl ($C_1$–$C_{10}$) or cycloakenyl ($C_1$–$C_{10}$) or furanylalkyl ($C_1$–$C_{15}$) alkylthioalkyli ($C_5$–$C_{15}$) or alkylene ($C_4$–$C_{10}$) or indolyl or pyridinyl or pyrrolinyl or quniolinyl or thienyl or tert-butoxycarbonyl amino or hydrogen or hydroxy protecting groups or functional groups which increase water solubility of the analog or amino protecting group or sulfhydryl protecting group or carbamat ($C_2$–$C_6$) or heteroaryl or crotyl.

What is claimed is:

1. A method of treating cancer or HIV comprising administering an effective dose of a compound of the general Formula I Formula I

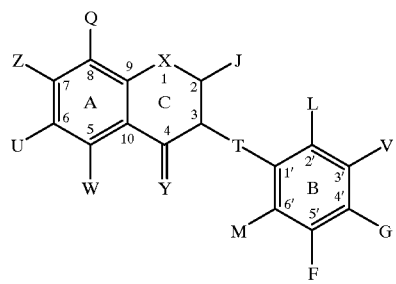

the 2-3 bond in ring C is a single or double bond, ring B and its substituents are attached at position 3 (at T) or at position 2 (at J) in ring C, X is S, N, P, C, O, a pharmaceutically acceptable metal or $CH_2$, Y is S, N, P, O, alkyl ($C_1$–$C_8$), alkyloxy ($C_1$–$C_8$), alkythio ($C_1$–$C_8$), aryloxy ($C_6$–$C_{10}$), alkoxycarbonyl ($C_2$–$C_8$), heterocycloalkoxy ($C_2$–$C_{10}$), pharmaceutically acceptable metal or $CH_2$,

19 one or more of L, V, G, F, M, W, U, Z, are Q are independently substituted by a prenylation provided that the prenylation not cyclize through the free OH group(s) at an ortho position to the prenylation, where the prenylation is prenteny ($-CH_2-CH=C(CH_3)_2$), geranyl ($-CH_2CH=C(Me)CH_2CH_2CH=C(Me)_2$), lavandulyl ($-CH_2-CH(C(CH_3)(=CH_2)-CH_2CH=C(CH_3)_2$, o-pentenyl (o-$CH_2-CH=C(CH_3)_2$), o-geranyl (o-$CH_2CH=C(Me)CH_2CH_2=CH(Me)_2$) o-lavandulyl (o-$CH_2-CH(C(CH_3(=CH_2)-CH_2CH=C(CH_3)_2$, or substituted pentenyl, geranyl and lavandulyl with hydroxy, alkyl ($C_1-C_8$), alkyloxy ($C_1-C_8$), alkylthio ($C_1-C_8$), aryloxy ($C_6-C_{10}$), alkoxycarbonyl ($C_2-C_8$), heterocycloalkoxy ($C_2-C_{10}$) or halogen, and on the ortho positions of these groups, it is substituted with H, veratryl, anisyl, epoxyangelyl, isobutanolyl, angelyl, 6-dimethylpyrane, formylloxy, isoamyl, 3-methylbutyl, -O-heterocycle ($C_2-C_{10}$), alkyloxy ($C_1-C_8$), alkylthio ($C_1-C_8$), aryloxy ($C_6-C_{10}$), alkoxycarbonyl ($C_2-C_8$), heterocycloalkoxy ($C_2-C_{10}$), amino, glycosides (1–10 sugar units), -O-glycosides (1–10 units), oxyacetic acids, Schiff Base, dialkylaminoalkyl ($C_1-C_{10}$), amino acid esters, flavan, aryl groups substituted with alkyl ($C_1-C_8$) or phenoxy or alkenyl ($C_3-C_8$), or phenyl substituted with one, two, or three groups each independently being hydroxy, halogen, alkynl ($C_2-C_8$), nitro, cyano or acetates, any position L, V, G, F, M, W, U, Z, or Q which is not prenylated as above is substituted to prevent internal cyclization of the prenylation, with H, alkyloxy ($C_1-C_8$), alkylthio ($C_1-C_8$), aryloxy ($C_6-C_{10}$), alkoxycarbonyl ($C_2-C_8$), heterocycloalkoxy ($C_2-C_{10}$), halogen, veratryl, anisyl, epoxyangelyl, isobutanolyl, angelyl, 6-dimethylpyrane, formylloxy, isoamyl, 3-methylbutyl, -O-heterocycle ($C_2-C_{10}$), alkyloxy ($C_1-C_8$), alkylthio ($C_1-C_8$), aryloxy ($C_6-C_{10}$), alkoxycarbonyl ($C_2-C_8$), heterocycloalkoxy ($C_2-C_{10}$), amino, glycosides (1–10 sugar units), -O-glycosides (1–10 units), oxyacetic acids, Schiff Base, dialkylaminoalkyl ($C_1-C_{10}$), amino acid esters, extended amines ($C_1-C_{10}$, $N_1-N_6$), sulphate esters, flavan, substituted flavan, aryl groups substituted with alkyl ($C_1-C_8$) or phenoxy or alkenyl ($C_3-C_8$), or phenyl substituted with one, two, or three groups each independently being hydroxy, halogen, alkynl ($C_2-C_8$), nitro, cyano or acetates, saturated or unsaturated aliphatic ($C_2-C_8$), cycloaliphatic ($C_1-C_{15}$), aromatic hydrocarbonyl ($C_1-C_{15}$), bridged cycloalkyl ($C_1-C_{10}$) or cycloakenyl ($C_1-C_{10}$) or furanylalkyl ($C_1-C_{15}$), alkylthioalkyl ($C_5-C_{15}$) or alkylene ($C_4-C_{10}$) or indolyl or pyridinyl or pyrrolinyl, or quinolinyl, or thienyl, or tert-butoxycarbonyl amino, hydrogen, hydroxy protecting groups, functional groups which increase water solubility, amino protecting group, sulfhydryl protecting group, carbamat ($C_2-C_6$), heteroaryl or crotyl to a mammal infected with HIV or for the treatment of symptoms of acquired immunodeficiency syndrome or cancer.

2. A method of treating cancer of HIV comprising administering an effective dose of a compound of the Formula II

20

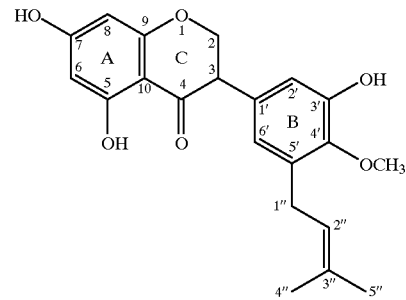

to a mammal infected with HIV or for the treatment of symptoms of acquired immunodeficiency syndrome or cancer.

3. A method of treating cancer of HIV comprising administering an effective dosage of a compound to a mammal infected with HIV or for the treatment of symptoms of acquired immunodeficiency syndrome or cancer wherein said compound has the general formula I Formula I

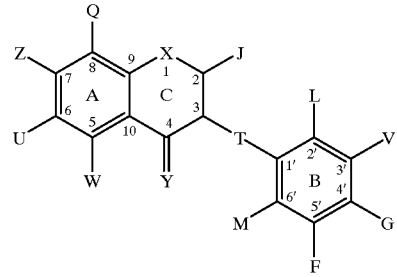

wherein:
the 2-3 bond in ring C is a single or double bond,
ring B and its substituents are attached at position 3 (at T) or at position 2 (at J) in ring C,
X is S, N, P, C, O, a pharmaceutically acceptable metal or $CH_2$,
Y is S, N, P, O, alkyl ($C_1-C_8$), alkyloxy ($C_1-C_8$), alkylthio ($C_1-C_8$), aryloxy ($C_6-C_{10}$), pharmaceutically acceptable metal or $CH_2$,
one or more of L, V, G, F, M, W, U, Z, are Q are independently substituted by a prenylation provided that the prenylation not cyclize through the free OH group(s) at an ortho position to the prenylation, where the prenylation is prenteny ($-CH_2-CH=C(CH_3)_2$), geranyl ($-CH_2CH=C(Me)CH_2CH_2CH=C(Me)_2$), lavandulyl ($-CH_2-CH(C(CH_3)(=CH_2)-CH_2CH=C(CH_3)_2$, o-pentenyl (o-$CH_2-CH=C(CH_3)_2$), o-geranyl (o-$CH_2CH=C(Me)CH_2CH_2=CH(Me)_2$) o-lavandulyl (o-$CH_2-CH(C(CH_3(=CH_2)-CH_2CH=C(CH_3)_2$, or substituted pentenyl, geranyl and lavandulyl with hydroxy, alkyl ($C_1-C_8$), alkyloxy ($C_1-C_8$), alkylthio ($C_1-C_8$), aryloxy ($C_6-C_{10}$), alkoxycarbonyl ($C_2-C_8$), heterocycloalkoxy ($C_2-C_{10}$) or halogen, and on the ortho positions of these groups, it is substituted with H, veratryl, anisyl, epoxyangelyl, isobutanolyl, angelyl, 6-dimethylpyrane, formylloxy, isoamyl, 3-methylbutyl, -O-heterocycle ($C_2-C_{10}$), alkyloxy ($C_1-C_8$), alkylthio ($c_1-C_8$), aryloxy ($C_6-C_{10}$), alkoxycarbonyl ($C_2-C_8$), heterocycloalkoxy ($C_2-C_{10}$), amino, glycosides (1–10 sugar units), -O-glycosides (1–10 units), oxyacetic acids, Schiff Base, dialkylaminoalkyl ($C_1$–$C_{10}$), amino acid esters, flavan, aryl groups substituted with alkyl ($C_1$–$C_8$) or phenoxy or alkenyl ($C_3$–$C_8$), or phenyl substituted with one, two, or three groups each independently being hydroxy, halogen, alkynl ($C_2$–$C_8$), nitro, cyano or acetates, any position L, V, G, F, M, W, U, Z, or Q which is not prenylated as above is substituted to prevent internal cyclization of the prenylation, with H, alkyloxy ($C_1$–$C_8$), alkylthio ($C_1$–$C_8$), aryloxy ($C_6$–$C_{10}$), alkoxycarbonyl ($C_2$–$C_8$), heterocycloalkoxy ($C_2$–$C_{10}$), halogen, veratryl, anisyl, epoxyangelyl, isobutanolyl, angelyl, 6-dimethylpyrane, formylloxy, isoamyl, 3-methylbutyl, -O-heterocycle ($C_2$–$C_{10}$), alkyloxy ($C_1$–$C_8$), alkylthio ($C_1$–$C_8$), aryloxy ($C_6$–$C_{10}$), alkoxycarbonyl ($C_2$–$C_8$), heterocycloalkoxy ($C_2$–$C_{10}$), amino, glycosides (1–10 sugar units), -O-glycosides (1–10 units), oxyacetic acids, Schiff Base, dialkylaminoalkyl ($C_1$–$C_{10}$), amino acid esters, extended amines ($C_1$–$C_{10}$, $N_1$–$N_6$), sulphate esters, flavan, substituted flavan, aryl groups substituted with alkyl ($C_1$–$C_8$) or phenoxy or alkenyl ($C_3$–$C_8$), or phenyl substituted with one, two, or three groups each independently being hydroxy, halogen, alkynl ($C_2$–$C_8$), nitro, cyano or acetates, saturated or unsaturated aliphatic ($C_2$–$C_8$), cycloaliphatic ($C_1$–$C_{15}$), aromatic hydrocarbonyl ($C_1$–$C_{15}$), bridged cycloalkyl ($C_1$–$C_{10}$) or cycloakenyl ($C_1$–$C_{10}$) or furanylalkyl ($C_1$–$C_{15}$), alkylthioalkyl ($C_5$–$C_{15}$) or alkylene ($C_4$–$C_{10}$) or indolyl or pyridinyl or pyrrolinyl, or quniolinyl, or thienyl, or tert-butoxycarbonyl amino, hydrogen, hydroxy protecting groups, functional groups which increase water solubility, amino protecting group, sulfhydryl protecting group, carbamat ($C_2$–$C_6$), heteroaryl or crotyl.

\* \* \* \* \*